(12) United States Patent
Lee

(10) Patent No.: US 9,695,381 B2
(45) Date of Patent: Jul. 4, 2017

(54) TWO STAGE HIGH SPEED CENTRIFUGES IN SERIES USED TO RECOVER OIL AND PROTEIN FROM A WHOLE STILLAGE IN A DRY MILL PROCESS

(71) Applicant: Lee Tech LLC, Fremont, CA (US)

(72) Inventor: Chie Ying Lee, Fremont, CA (US)

(73) Assignee: Lee Tech, LLC, Fremont, CA (US)

( * ) Notice: Subject to any disclaimer, the term of this patent is extended or adjusted under 35 U.S.C. 154(b) by 0 days.

(21) Appl. No.: 13/844,506

(22) Filed: Mar. 15, 2013

(65) Prior Publication Data

US 2014/0147897 A1    May 29, 2014

Related U.S. Application Data

(60) Provisional application No. 61/729,998, filed on Nov. 26, 2012, provisional application No. 61/739,622, filed on Dec. 19, 2012.

(51) Int. Cl.

| | | |
|---|---|---|
| *C12M 1/12* | (2006.01) | |
| *C11B 3/00* | (2006.01) | |
| *C07K 1/36* | (2006.01) | |
| *C11B 1/10* | (2006.01) | |
| *C11B 3/16* | (2006.01) | |
| *A23K 10/38* | (2016.01) | |
| *A23K 50/75* | (2016.01) | |
| *A23K 50/30* | (2016.01) | |

(52) U.S. Cl.
CPC .............. *C11B 3/003* (2013.01); *A23K 10/38* (2016.05); *A23K 50/30* (2016.05); *A23K 50/75* (2016.05); *C07K 1/36* (2013.01); *C11B 1/10* (2013.01); *C11B 1/108* (2013.01); *C11B 3/16* (2013.01); *Y02P 60/873* (2015.11)

(58) Field of Classification Search
CPC ....... C12M 21/12; C12M 47/10; C12M 47/12
See application file for complete search history.

(56) References Cited

U.S. PATENT DOCUMENTS

| | | |
|---|---|---|
| 2,600,903 A | 6/1952 | Miller |
| 3,058,887 A | 11/1958 | Platt et al. |
| 3,054,676 A | 9/1962 | Lauhoff et al. |
| 3,786,078 A | 1/1974 | Smith et al. |
| 3,827,423 A | 8/1974 | Bolitho |
| 3,973,043 A | 8/1976 | Lynn |
| 3,975,546 A | 8/1976 | Stahmann |
| 4,042,172 A * | 8/1977 | Nozdrovsky ............. B04B 3/04 494/53 |

(Continued)

FOREIGN PATENT DOCUMENTS

| | | |
|---|---|---|
| DE | 4239342 A1 | 5/1994 |
| EP | 0772978 B1 | 11/1999 |

(Continued)

OTHER PUBLICATIONS

International Search Report and Written Opinion from PCT Application No. PCT/US15/47577, (Jan. 19, 2016).

(Continued)

*Primary Examiner* — William H Beisner
(74) *Attorney, Agent, or Firm* — Haverstock & Owens LLP

(57) ABSTRACT

Methods of and devices for recovering oil and protein and increasing production yields using two centrifuges in series or a centrifuge with dual oil and protein separating functions in a dry mill are provided.

17 Claims, 16 Drawing Sheets

(56) References Cited

U.S. PATENT DOCUMENTS

| | | | |
|---|---|---|---|
| 4,171,383 A | 10/1979 | Chwalek et al. | |
| 4,255,518 A | 3/1981 | Muller et al. | |
| 4,313,061 A | 1/1982 | Thomas | |
| 4,341,713 A | 7/1982 | Stolp et al. | |
| 4,361,651 A | 11/1982 | Keim | |
| 4,396,161 A | 8/1983 | Ruokolainen et al. | |
| 4,517,022 A | 5/1985 | Harvey | |
| 4,635,864 A | 1/1987 | Peterson et al. | |
| 5,177,008 A | 1/1993 | Kampen | |
| 5,244,159 A | 9/1993 | Newman | |
| 5,248,099 A | 9/1993 | Lahner et al. | |
| 5,364,335 A * | 11/1994 | Franzen et al. | 494/15 |
| 6,190,462 B1 | 2/2001 | Markland et al. | |
| 6,254,914 B1 | 7/2001 | Singh et al. | |
| 6,274,358 B1 | 8/2001 | Holtz et al. | |
| 6,899,910 B2 | 5/2005 | Johnston et al. | |
| 7,563,469 B1 | 7/2009 | Navarro et al. | |
| 7,858,140 B2 | 12/2010 | Paustian et al. | |
| 9,012,191 B2 | 4/2015 | Lee | |
| 2002/0122944 A1 | 9/2002 | Ogle et al. | |
| 2004/0009160 A1 | 1/2004 | Villamar | |
| 2004/0071757 A1 | 4/2004 | Rolf | |
| 2004/0087808 A1 | 5/2004 | Prevost et al. | |
| 2004/0187863 A1 | 9/2004 | Langhauser | |
| 2004/0258782 A1 | 12/2004 | Hoffman et al. | |
| 2005/0009133 A1 | 1/2005 | Johnston et al. | |
| 2005/0100996 A1 | 5/2005 | Lantero, Jr. et al. | |
| 2005/0170067 A1 | 8/2005 | Shao et al. | |
| 2005/0249837 A1 | 11/2005 | Massimino et al. | |
| 2006/0292677 A1 | 12/2006 | Ostrander | |
| 2007/0184541 A1 | 8/2007 | Karl et al. | |
| 2007/0210007 A1 | 9/2007 | Scheimann et al. | |
| 2008/0210541 A1 | 9/2008 | Wenger et al. | |
| 2009/0029432 A1 | 1/2009 | Abbas et al. | |
| 2009/0061490 A1 | 3/2009 | Edwards et al. | |
| 2009/0093027 A1 | 4/2009 | Balan et al. | |
| 2009/0227004 A1 | 9/2009 | Dale | |
| 2010/0028484 A1 | 2/2010 | Kriesler et al. | |
| 2010/0082312 A1 | 4/2010 | Macharia | |
| 2010/0093860 A1 | 4/2010 | Boon et al. | |
| 2010/0159547 A1 | 6/2010 | Faulconbridge | |
| 2010/0159552 A1 | 6/2010 | Benson et al. | |
| 2010/0196994 A1 | 8/2010 | van Leeuwen et al. | |
| 2010/0260918 A1 | 10/2010 | Wang | |
| 2011/0086149 A1 * | 4/2011 | Bootsma | 426/541 |
| 2011/0100359 A1 | 5/2011 | North | |
| 2011/0123657 A1 | 5/2011 | Vandenbroucke et al. | |
| 2011/0150853 A1 | 6/2011 | Mann et al. | |
| 2011/0177560 A1 | 7/2011 | Galvez, III et al. | |
| 2011/0223307 A1 | 9/2011 | Bertoldo de Barros et al. | |
| 2011/0250312 A1 | 10/2011 | Lewis | |
| 2011/0269185 A1 | 11/2011 | David | |
| 2011/0283602 A1 | 11/2011 | Gallop et al. | |
| 2012/0077232 A1 | 3/2012 | Budaraju et al. | |
| 2012/0077244 A1 | 3/2012 | Budaraju et al. | |
| 2012/0107454 A1 | 5/2012 | Hoffman et al. | |
| 2012/0125859 A1 | 5/2012 | Collins | |
| 2012/0168387 A1 | 7/2012 | Tran et al. | |
| 2012/0199531 A1 | 8/2012 | Winsness | |
| 2012/0244590 A1 | 9/2012 | Lee | |
| 2012/0245123 A1 | 9/2012 | Lopez Pedrosa et al. | |
| 2012/0252065 A1 | 10/2012 | Rozenszain et al. | |
| 2012/0270275 A1 | 10/2012 | Fenton et al. | |
| 2013/0121891 A1 | 5/2013 | Dieker | |
| 2013/0206342 A1 | 8/2013 | Dahmes | |
| 2013/0224333 A1 | 8/2013 | Nanjundaswamy et al. | |
| 2013/0236936 A1 | 9/2013 | Lee | |
| 2013/0288376 A1 | 10/2013 | Lee | |
| 2013/0316041 A1 | 11/2013 | Maranz | |
| 2013/0344045 A1 | 12/2013 | Faure | |
| 2014/0053829 A1 | 2/2014 | Lee | |
| 2014/0102950 A1 | 4/2014 | Bethke et al. | |
| 2014/0186868 A1 | 7/2014 | Siegert et al. | |
| 2014/0242251 A1 * | 8/2014 | Bootsma | 426/624 |
| 2014/0319066 A1 | 10/2014 | LosCascio | |

FOREIGN PATENT DOCUMENTS

| | | |
|---|---|---|
| GB | 852995 A | 11/1960 |
| WO | 01/14595 A2 | 3/2001 |
| WO | 2012/075481 A1 | 6/2012 |
| WO | WO 2012145230 A1 * | 10/2012 |
| WO | 2012160191 A2 | 11/2012 |

OTHER PUBLICATIONS

Blog, Birdworms & Buttermilk, Extracting Chlorophyll from Leafy Greens; available at: http://birdworms.com/2010/06/26/extractingchlorophyllfromleafygreens/; accessed on Oct. 6, 2016; published on Jun. 2010.

Timbekova et al.., Chemistry and Biological Activity of Triterpenoid glycosides from Medicago.

Gonzalez-Martin, Use of NIRS technology with a remote reflectance fibre-optic probe for predicting mineral composition(Ca, K, P, Fe, Mn, Na, Zn), protein and moisture in alfalfa; Anal Bioanal Chem (2007) 387:2199-2205.

Singh et al., Effect of Corn Oil on Thin Stillage Evaporators,Cereal Chemistry, pp. 846-849, 1999.

Heist, A Guide to Successful Yeast Propagatiion, Ethanol Producer Magazine, 2008.

Shahina Z. et al., "Variation of Protease Production by the Bacteria (*Bacillus fastidiosus*) and the Fungus (*Aspergillus funiculosus*)", Journal of Microbiology Research [online], 2013 [retrieved on Oct. 17, 2016], vol. 3, issue 4, retrieved from the Internet: <DIO: 10.5923//j.microbiology.2013030402>, pp. 135-142, see entire documents, especially p. 135.

International Search Report from PCT/US16/38436 dated Oct. 31, 2016.

* cited by examiner

TWO STAGE HIGH SPEED CENTRIFUGES IN SERIES USED TO RECOVER OIL AND PROTEIN FROM A WHOLE STILLAGE IN A DRY MILL PROCESS

CROSS-REFERENCE TO RELATED APPLICATIONS

This application claims priority from U.S. Provisional Patent Application Ser. No. 61/729,998, filed Nov. 26, 2012 and entitled "TWO STAGE HIGH SPEED CENTRIFUGES IN SERIES USED TO RECOVER OIL AND PROTEIN FROM A WHOLE STILLAGE IN A DRY MILL PROCESS," and U.S. Provisional Patent Application Ser. No. 61/739,622, filed Dec. 19, 2012 and entitled "TWO STAGE HIGH SPEED CENTRIFUGES IN SERIES USED TO RECOVER OIL AND PROTEIN FROM A WHOLE STILLAGE IN A DRY MILL PROCESS," which are hereby incorporated herein by reference in their entirety for all purposes.

FIELD OF THE INVENTION

The present invention relates to methods of and devices for producing oil, protein, and alcohol in a dry mill system. More specifically, the present invention relates to a system using two centrifuges in series or a dual function centrifuge to recover and improve yields of the by-product oil and protein in dry mill ethanol plants.

BACKGROUND OF THE INVENTION

FIG. 1 is a typical dry mill process having a back-end oil recovery system. FIG. 2 is a typical dry mill process with a back-end oil and protein recovery system. FIG. 3 is a dry mill process having a front-end dewatering mill system and a front-end oil recovery system. FIG. 3A is a dry mill process having a front-end dewatering mill system, a front-end oil recovery system, and a back-end protein recovery system.

The typical methods of producing alcohols from grains generally follow similar procedures depending on whether the process is operated under wet or dry conditions. Wet mill corn processing plants convert corn grains into several different co-products, such as germ (for oil extraction), gluten feed (high fiber animal feed), gluten meal (high protein animal feed), and starch-based products, such as ethanol, high fructose corn syrup, food, and industrial starch. Dry grind ethanol plants convert corn into two products, including ethanol and distiller's grains with soluble. If it is sold as wet animal feed, distiller's wet grains with soluble is referred to as DWGS. If it is dried for animal feed, distiller's dried grains with soluble is referred to as DDGS. In the standard dry grind ethanol process, one bushel of corn yields approximately 8.2 kg (approximately 17 lbs.) of DDGS in addition to approximately 10.3 liters (approximately 2.75 gal) of ethanol. These co-products provide a critical secondary revenue stream that offsets a portion of the overall ethanol production costs. DDGS is normally sold as a low value animal feed even though that the DDGS contains 11% oil and 33% protein. Some plants start to modify the typical process to separate the valuable oil and proteins from the DDGS. Currently, some plants recover oil from syrup by one stage centrifuge, such as a decanter or a disc centrifuge.

Because the costs of wet grinding mills are so prohibitive, some alcohol plants prefer to use a simpler dry grinding process. FIG. 1 is a flow diagram of a typical dry grind ethanol producing process 10. As a general reference point, the dry grind ethanol process 10 is divided into a front-end process and a back-end process. The part of the process 10 that occurs prior to a step of distilling 14/fermenting 13 is considered as the "front-end" process and the part that occurs after the step of distilling 14/fermenting 13 is considered as the "back-end" process. The front-end process of the process 10 begins with a grinding step 11 in which dried whole corn kernels are passed through a hammer mill to be ground into corn meal or a fine powder. The screen openings in the hammer mills are typically of size #7 or about 2.78 mm, which result in a wide spread of particle sizes distribution. The particle sizes mentioned above are as small as 45 micron and as large as 2 to 3 mm. The ground meal at the grinding step 11 is mixed with water to create slurry. A commercial enzyme called alpha-amylase is added (not shown) to the slurry.

In a liquefying step 12, the slurry is heated to approximately 120° C. for about 0.5 to 3 minutes in a pressurized jet cooking process to gelatinize (solubilize) the starch in the ground meal. In some typical processes, a jet cooker is not used and a longer tank holding time is used instead. The pH value at the liquefying step 12 is adjusted to about 5.8 to 6 and the temperature is maintained between 50° C. to 105° C. to convert the insoluble starch in the slurry to become a soluble starch. The stream after the liquefying step 12 has about 30% dry solids (DS) and all other components that are in the corn kernels, including sugars, protein, fiber, starch, germ, grit, oil and salt. There are generally three types of solid particle sizes larger than 50 micron in the liquefying stream: fiber, germ, and grit, which have about the same particle size distributions in all three types of solids.

The liquefying step 12 is followed by a simultaneous saccharifying and fermenting step 13. This simultaneous step 13 is referred in the industry as "Simultaneous Saccharification and Fermentation" (SSF). In some commercial dry grinding ethanol processes, saccharification and fermentation occur separately (not shown). Both individual saccharification and SSF take as long as about 50 to 60 hours. Fermentation converts the sugar to alcohol using a fermenter. Subsequent to the saccharifying and fermenting step 13 is a distilling (and dehydrating) step 14, which utilizes a still to recover alcohol.

Next to the distilling step 14 is a fiber separating step 15. The fiber separating step 15 centrifuging the "whole stillage" produced at the distilling step 14 to separate the insoluble solids ("wet cake") from the liquid ("thin stillage"). The "wet cake" includes fibers (per cap, tip cap, and fine fibers), grits, germ particles and some proteins. The liquid from the centrifuge contains about 6% to 8% of DS, which contains mainly oil, germs, fine fibers, fine grits, protein, and soluble solids from the fermenter and ash from corns. The whole stillage in some plants with an average of about 14% of DS is fed to the first stage evaporator that is concentrated to 16~25% DS before feeding to the fiber separating step 15.

The thin stillage from the fiber separating step 15 is divided into two streams. The first stream containing about 30 to 40% of the flow is recycled back (as a "back-set" stream) to be mixed with corn flour in a slurry tank at the beginning of the liquefying step 12. The second stream that contains the rest of the flow (about 60 to 70% of the total flow) enters evaporators in an evaporating step 17 to boil away some water moisture leaving oil, protein (gluten and yeast), and a thick syrup that contains mainly soluble (dissolved) solids in the corn. The back-set water is used as part of cooking water in the liquefying step 12 to cut the fresh water consumption as well as save evaporating energy and equipment costs.

The concentrated slurry is able to be subjected to an optional oil recovering step 16, whereat the slurry can be centrifuged to separate oil out from the syrup. The oil is able to be sold as a separate high value product. The oil yield is normally about 0.4 lbs./Bu of corn with a content of high free fatty acids (around 15% FFA). This back-end oil recovering system recovers only about ¼ of the oil in the corn. About one-half of the oil inside the corn kernel remains inside the germ after the fermenting/distilling step 13/14. Only about 1 lb./Bu of free oil is available to be recovered from the syrup and the other half (about 1 lb./Bu oil) still remains inside the germ oil cell. Most of the not recovered oil (inside the germ oil cell) goes out with decanter cake (DDG).

About 0.5 lb./Bu of the oil in the syrup (thin stillage) is trapped/absorbed in the fine fibers or forms an emulsion layer (having a density around 1 g/ml) with proteins, which cannot be separated in a typical dry grind process using one stage centrifuges. The emulsion layer stays and builds up inside the machine, which affects the oil separation inside the centrifuge. There are ways to break emulsion (decrease amount of emulsion) and increase the oil yield by adding chemicals (e.g., emulsion breaking chemicals and emulsion breakers), adding alcohol to an extraction step, or heating to a higher temperature. Although the above three methods are effective in reducing emulsions, each of the methods has its drawbacks. Although adding chemicals, such as emulsion breaker, is able to improve the separation efficiency in some degrees, chemicals are costly and the DDGS product can be contaminated by the added chemicals. Providing heat or raising the feed temperature at the centrifuge to break the emulsion is another way to improve the separation efficiency, but the temperature affects the quality of oil and DDGS (mainly higher free fatty acid and darker color). Adding an alcohol to break the emulsion also improves the separation and increases the oil yield, but it needs exploration proof equipment and costly operations. All these improvements only increase the oil yield from an average of 0.4 lbs./Bu to about average 0.6 lbs./Bu. About 0.4 lbs/Bu of the oil trapped/absorbed is still not able to be recovered. The oil/protein emulsion formed during the whole dry mill process is the main reason having a low oil yield in the back-end oil recovery system.

An oil and protein recovery process (PCT/US09/45163, filed on May 26, 2009; titled "METHODS FOR PRODUCING A HIGH PROTEIN CORN MEAL FROM A WHOLE STILLAGE BYPRODUCT AND SYSTEM THEREFORE," which is incorporate by reference in its entirety for all purposes), is developed by adding an oil/protein separating step to break this oil/protein emulsion in the thin stillage. As shown in the process 20 of FIG. 2, the front-end process is the same as the existing dry mill process described in the FIG. 1. The process changes its procedures after the fiber separating step 15, which is part of the back-end process. The oil/protein separating step 21 is added between the fiber separating step 15 and the evaporating step 17. A high G force centrifuge, such as nozzle centrifuges and disc decanter, are able to be used at this step instead of other types of disc centrifuges or lower G force decanter, because the high G force nozzle is more effective in breaking the oil/protein emulsion. The thin stillage from the fiber separating step 15 is fed to the oil/protein separating centrifuge step 21. The oil/protein emulsion is broken up by the high G force inside the centrifuge. The overflow discharge (light phase) that contains the free oil is discharged from the top of nozzle centrifuge with a portion of a liquid as an overflow. The underflow discharge (heavy phase) that contains protein and fine fiber, which is heavier than the liquid, is discharge from the nozzle with a portion of the liquid in slurry. The oil/protein emulsion is broken up under a high G force inside the disc stock. The oil that is trapped and/or absorbed by the fine fiber is able to be released by using the density difference of the oil (0.9 gram/ml), protein (1.05 gram/ml), and fiber (1.1 gram/ml). The overflow is then fed to an evaporator step 17 to be concentrated to have a 25 to 40% of DS (forming a semi-concentrated syrup).

Next, the semi-concentrated syrup is sent to the back-end oil recovery system step 16 for oil recovery. The overflow stream from oil/protein separating step 21 contains less protein, so it has less chance to form oil/protein emulsion during the evaporator stage. The oil yield with this system reaches 0.9 lb./Bu. The de-oil syrup from the back-end oil recovery step 16 is able to be further concentrated in an evaporator to have a higher syrup concentration with as high as 75% of DS. The de-oil syrup with a low protein content can avoid fouling at the evaporator. The underflow from oil/protein separating step 21 goes to a protein dewatering step 22 for protein recovery. The separated protein cake from protein dewatering step 22 having a content of less than 3% oil is sent to a protein dryer at a protein drying step 23 to produce a high value protein meal, which has a protein content of 50%. The liquid from the protein dewatering step 22 is sent back to the front-end as a back-set liquid that is used as part of cooking water in the liquefying step 12.

The process described in the patent application (PCT/US12/30337; file on May 23, 2012; titled "DRY GRIND ETHANOL PRODUCTION PROCESS AND SYSTEM WITH FRONT END MILLING METHOD" is incorporate by reference in its entirety for all purposes. The process having a front dewatering mill and a front oil recovery system is shown in a process 30 of FIG. 3. In the process 30, a dewatering mill system is added to a liquefying step 32. The step 32 is followed by front-end oil recovery steps 31 and 33, such that oil is able to be recovered in the front-end (i.e., before the fermenting step 13). A three phase nozzle centrifuge at step 31 is used to separate the content into a light phase, a heavy phase, and a nozzle phase. The heavy phase contains protein. The light phase contains oil, emulation, and germs, which are from the liquefied starch solution. The light phase is subsequently sent to an oil polish centrifuge step 33 to recover pure oil. The oil that is recovered at the front-end has a much lighter color, lower fatty acid, and is able to be more easily separated in the centrifuge, because a higher liquid density and less oil/protein formation is resulted by using this process. However, the oil yields only increased to 0.4 lb./Bu.

About ¼ of the oil (about 0.5 lb./Bu) in the germ is released during the fermenting step 13 and distilling step 14. A back-end oil recovering step 16 is used to recover more oil that is not released before the fermenting step 13 and distilling step 14. This combined front-oil recovering step 16 and back-end oil recovery step 31 can generate 0.4 lb./Bu oil at the front-end and 0.3 to 0.6 lb./Bu oil in the back-end depending on the type of emulsion breaking step used.

As shown in FIG. 3A, the protein recovering system is added to the system of FIG. 3. The system in FIG. 3A removes, recovers, and produces protein meal and increases the back-end oil yield by avoiding the formation of oil/protein emulsion during the evaporation process, which is also described in the U.S. Provisional Patent Application Ser. No. 61/692,593, filed Aug. 23, 2012 and entitled "A SYSTEM FOR AND METHOD OF SEPARATING OIL AND PROTEIN FROM GRAINS USED FOR ALCOHOL PRODUCTION," which is incorporated herein by reference in its entirety for all purposes. The oil/protein separating step 21, the protein dewatering step 22 and protein drying step 23 are added to the system of FIG. 3 to become the system of FIG. 3A. The protein drying step 23 (very high equipment cost) can be eliminated if producing protein meal is not needed. The protein wet cake from the protein dewatering step 22 is mixed with syrup from the evaporating step 17 and DDG cake from the fiber separating step 15 to produce DDGS by-product. The oil in the back-end increases to 0.5 to 0.8 lb./Bu depending on the number of dewater milling steps in the front-end.

Still referring to FIG. 3A, a two phases (Clarifier) nozzle centrifuge is used to effectively break the bonds between oil and protein and release the oil that is trapped/absorbed in the fine fiber. The oil (lighter than liquid) is discharged with the liquid in a slurry form as overflow discharge. The protein and fine fiber (heavy than liquid) are discharged with the liquid in slurry form as nozzle flow discharge (underflow). The overflow discharge contains free oil, oil/protein emulsion, and germ particles, which is used as a back-set stream to recycle back to the front-end. Accordingly, the oily stream (contained in the overflow) in the back-end process is able to going back to the front-end with the back-set stream to be recovered by the front end oil recovering step 31. In the typical dry mill process, two separate oil recovery systems (one in the front-end step 31 and one in the back-end step 16) are needed.

SUMMARY OF THE INVENTION

Methods of and devices for recovering oil and protein and increasing production yields using two centrifuges in series or a centrifuge with dual functions in dry mill ethanol plants are provided. In an aspect, a method of recovering oil from a thin stillage comprises using a three phase disc centrifuge to recover oil, an oil/protein/germ emulsion mixture, or a combination thereof from a thin stillage or a concentrated thin stillage and breaking the oil/protein/germ emulsion mixture and recovering the oil from the oil emulsion mixture using an oil polish centrifuge.

In another aspect, a dry mill system comprises fermenting, after fermenting, separating a thin stillage to a light phase portion, a heavy phase portion, and an underflow discharge portion using a first separating device, and obtaining an oil from the light phase portion using a second separating device.

In some embodiments, the first separating device comprises a three-phase nozzle centrifuge. In other embodiments, the first separating device comprises a disc decanter. In some other embodiments, the disc decanter comprises a three-phase decanter. In some embodiments, the second separating device comprises a oil-polishing centrifuge. In other embodiments, the dry mill process further comprises obtaining protein using a protein recovery system. In some other embodiments, the protein recovery system comprises a protein separating device and protein dryer. In some embodiments, the dry mill process further comprises dewater milling after the fermenting. In other embodiments, the dry mill process further comprises recovering germs after the fermenting. In some other embodiments, the dry mill process further comprises sending the underflow discharge portion to a front-end process before fermenting as a back-set stream. In some embodiments, the dry mill process further comprises sending the heavy phase portion to recover oil. In other embodiments, the dry mill process further comprises condensing the heavy phase portion using an evaporator to generate a syrup.

In some other embodiments, the dry mill process further comprises separating the syrup to an organic compound rich portion and an inorganic compound rich portion. In some embodiments, the dry mill process further comprises making a plant food using the inorganic compound rich portion. In other embodiments, the dry mill process further comprises making an animal food using the organic compound rich portion. In some other embodiments, the dry mill process further comprises separating a whole stillage after the fermenting to a solid portion and a liquid portion. In some embodiments, the dry mill process further comprises sending the solid portion to a dewater milling device.

In some other embodiments, the dry mill process further comprises sending the liquid portion to the first separating device. In other embodiments, the dry mill process further comprises separating germs from fiber after fermenting and before separating the thin stillage to the light phase portion, the heavy phase portion, and the underflow discharge portion. In some other embodiments, the dry mill process further comprises adding a concentrated syrup to increase a density of a heavy media having a density higher than the germs. In some embodiments, the concentrated syrup is generated after the separating the thin stillage to the light phase portion, the heavy phase portion, and the underflow discharge portion. In other embodiments, the dry mill process further comprises recovering the germs and send the germs to a front-end process before the fermenting.

In another aspect, a back-end two centrifuges dry mill system comprises a three-phase nozzle centrifuge and an oil polishing centrifuge after a fermenter. In some embodiments, the system comprises an emulsion breaking device fluidly couples with the three-phase nozzle centrifuge. In other embodiments, the system further comprises an oil polishing centrifuge fluidly couples with the emulsion breaking device. In some other embodiments, the system further comprises a liquid/solid separating device couples with the fermenter and the three-phase nozzle centrifuge, wherein the liquid/solid separating device located after the fermenter and before the three-phase nozzle centrifuge. In some other embodiments, the liquid/solid separating device receives a whole stillage and separates the whole stillage into a solid portion and a liquid portion. In other embodiments, the system comprises a dewater milling device receives the solid portion from the liquid/solid separating device.

In some other embodiments, the liquid portion is received by the three-phase nozzle centrifuge. In some embodiments, the three-phase nozzle centrifuge generates a underflow discharge, wherein the underflow discharge is used as a back-set stream. In other embodiments, the back-set stream is sent back to a front-end process before the fermenter. In some other embodiments, the three-phase nozzle centrifuge generates a heavy phase comprises de-oiled germs and protein. In some embodiments, the system further comprises an evaporator receives the heavy phase from the three-phase nozzle centrifuge. In some other embodiments, the system further comprises an oil recovery system receives an concentrated solution from the evaporator for oil recovery. In some embodiments, the three-phase nozzle centrifuge generates a heavy phase, wherein the heavy phase is used as a back-set stream at a front-end process before the fermenter. In other embodiments, the three-phase nozzle centrifuge generates a underflow discharge, wherein the underflow discharge is sent to an evaporator.

In some other embodiments, the three-phase nozzle centrifuge generates a heavy phase, wherein the heavy phase is sent to a protein recovery system. In some embodiments, the three-phase nozzle centrifuge generates a underflow discharge, wherein the underflow discharge is sent to a protein recovery system. In other embodiments, the underflow discharge is sent to an oil-protein separating device. In some other embodiments, the system further comprises a germ/fiber separating system located between the fermenter and the three-phase nozzle centrifuge.

In another aspect, a method of oil producing in a dry mill comprises, after fermenting, separating a whole stillage to a solid portion comprising fiber and germs and a liquid portion comprising a thin stillage, separating the fiber from the germs, sending the germs to a process before fermenting, and obtaining the oil from the thin stillage.

In some embodiments, the method further comprises dewater milling the solid portion. In other embodiments, the method further comprises making a pH value between 7-9. In some embodiments, the oil is obtained by using an oil polishing centrifuge.

In another aspect, a three-phase disc decanter comprises an oil recovering portion, and an protein recovering portion. In some embodiments, the three-phase disc decanter further comprises a rotating bowl. In other embodiments, the rotating bowl comprises a first disc stock and a second disc stock, wherein the first disc stock is different from the second disc stock. In some other embodiments, the three-phase disc decanter has a disc height/disc diameter ratio larger than 1. In some embodiments, the three-phase disc decanter further comprises a heavy phase outlet, a light phase outlet, and a solid outlet.

DETAILED DESCRIPTION OF THE PREFERRED EMBODIMENTS

Figure 1:
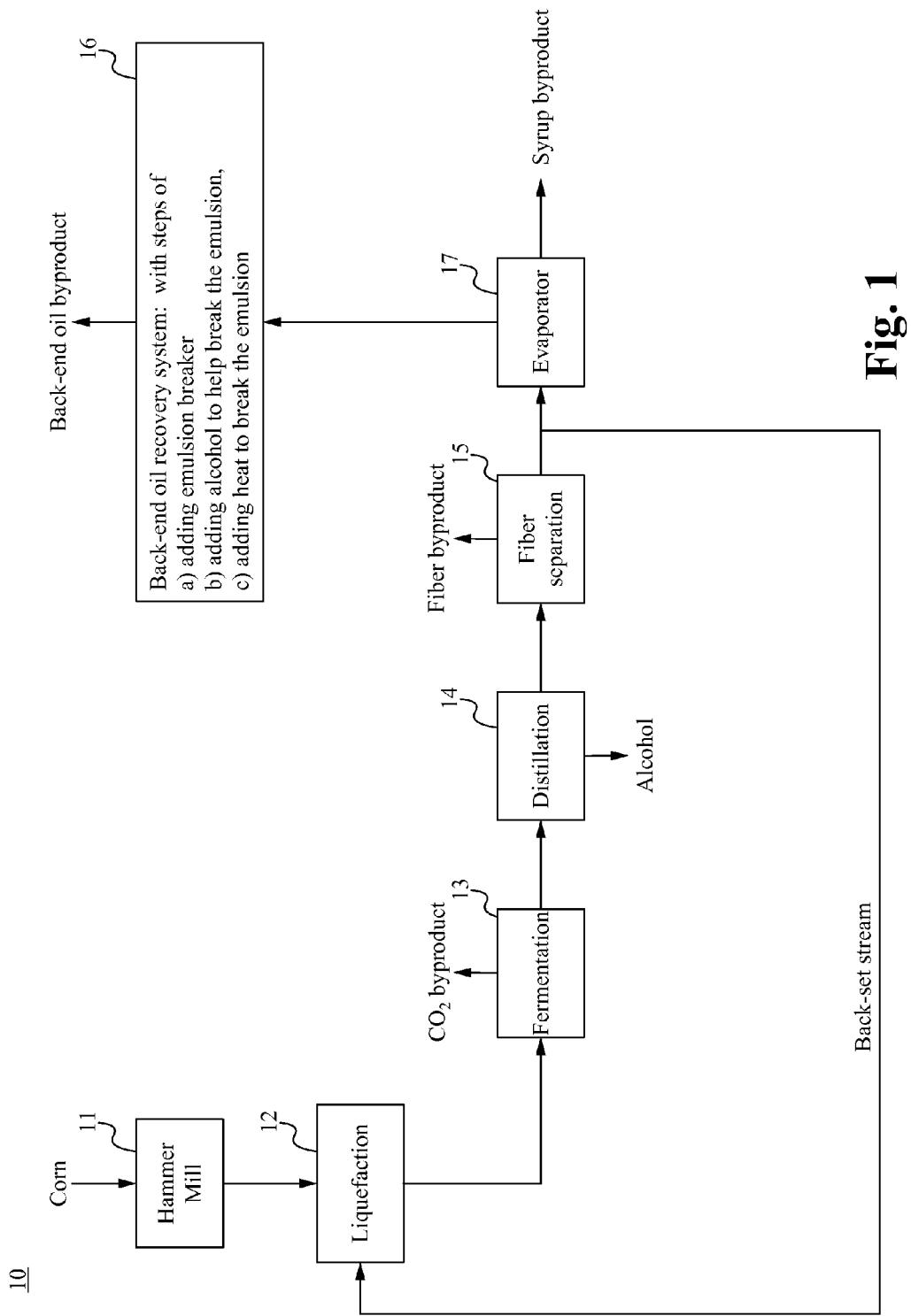
FIG. 1 is a typical dry mill process having a back-end oil recovery system.
Figure 2:
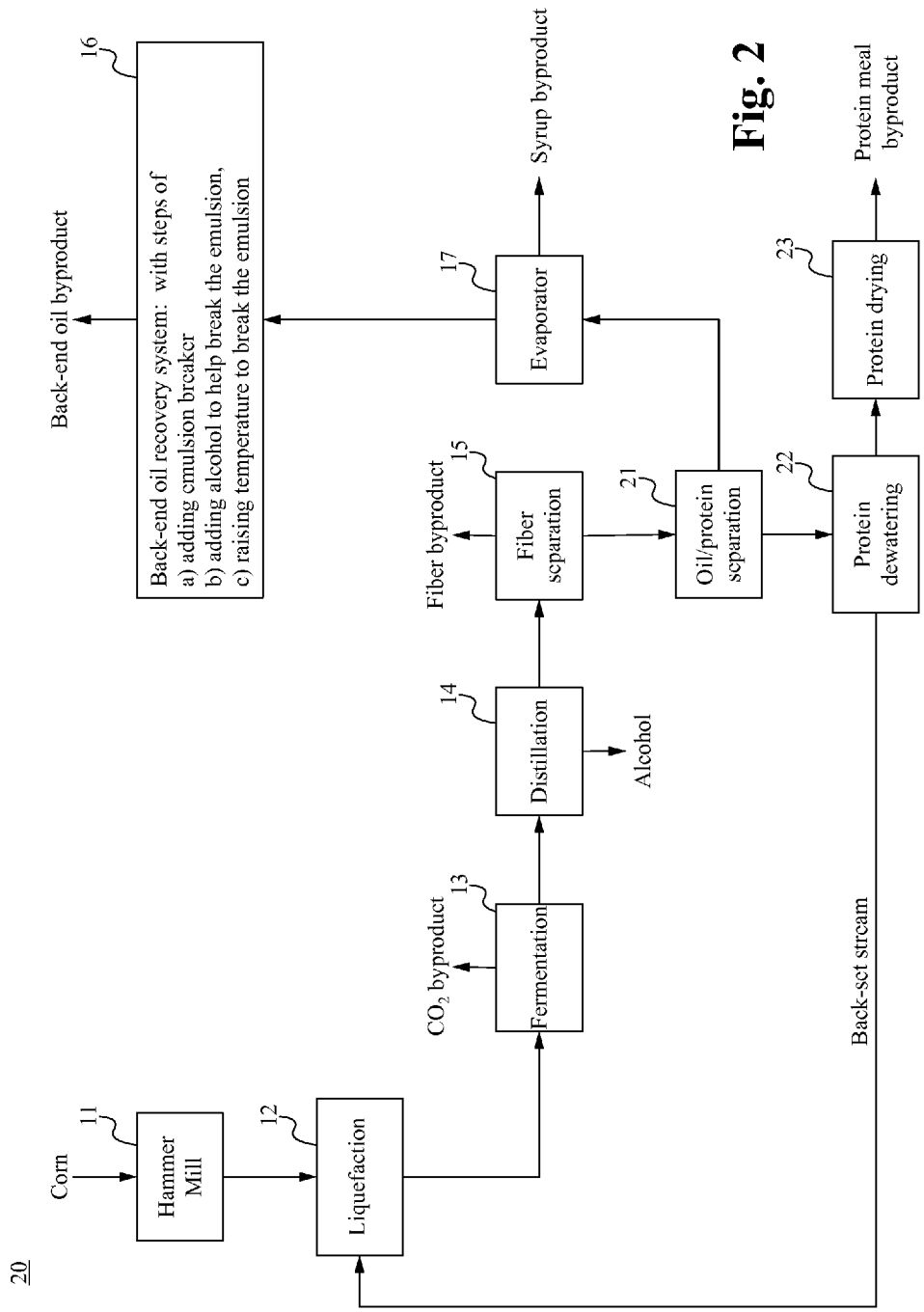
FIG. 2 is a typical dry mill process having a back-end oil and protein recovery system.

Processes described in FIGS. 4-8 are included as part of the back-end process. In other words, a fermenting step is able to be included prior the distilling step 24 of FIGS. 4-8. In some embodiments, the front-end process of the FIGS. 4-8 are able to be the same or similar to the front-end process described in the FIG. 1-3A.

Several disc centrifuges and decanters are developed to improve the oil and protein recovery yield and process. For example, a three-phase nozzle centrifuge (as shown in FIG. 9) is developed to separate/divide the thin stillage into three streams, including a) the light phase (mainly oil and emulsion/fine germ particles), b) the heavy phase (mainly clean liquid containing less oil and solid), and c) the underflow discharge (mainly high concentrated protein and fine fiber with small amount of liquid as the heavy slurry. In another example, a three-phase disc decanter (shown in FIG. 10) is developed to separate the thin stillage (or concentrated syrup) into three streams, including a) the light phase (mainly containing oil and emulsion/fine germ particles), b) the heavy phase (mainly containing clean liquid with much less oil and protein), and c) the cake phase discharge (mainly containing protein and fine fiber in a dry cake form). The processes in FIGS. 4-8, for recovering oil and protein from the whole stillage, are modified and are able to be used in conjunction with those two exemplary centrifuges (i.e., the three-phase nozzle centrifuge and three-phase disc decanter) to increase the oil and protein yield and quality.

Although a high G-force Clarifier (two-phase nozzle centrifuge) is able to be used to break the oil/protein emulsion (bonds between oil and protein) and also releases the oil trapped/absorbed in the fine fiber, both separated phases (oil-rich phase as an overflow phase and a protein-rich phase as an underflow phase) are both in a slurry form.

To improve from the typical devices and processes, three-phase nozzle centrifuges and decanters are disclosed, which are able to produce oil/emulsion/fine germ particle in a thick (very little liquid content) light phase instead of oily (soupy) overflow. Processes described in FIGS. 4-8 are able to be used in conjunction with the three-phase nozzle centrifuge and decanter for separating the thin stillage into three-streams instead of two streams of the typical clarified nozzle centrifuge.

In the following, the three-phase nozzle centrifuges and decanters are described in accordance with some embodiments of the present invention. FIG. 9 is a cross-sectional view of a three-phase nozzle centrifuge 900 in accordance with some embodiments of the present invention. In some embodiments, the feed come from the bottom 902 of the centrifuge 900 through the feed nozzle 921 and an acceleration chamber 903 into the inside radius of disc stock area 904. The oil, oil/protein emulsion, and fine germ particles (lighter than liquid) float in the smallest radius area 905 then are scooped by an adjustable skimmer 906, which is discharged as a light phase on top of the centrifuge 900. The liquid that carries the heavy solid (having a density higher than the liquid), such as fine fibers that trap/absorb some oil and oil/protein emulsion, enter through the open space 907 between the two disc from the inter radius of the disc 908 to the outer radius of disc 909. The oil that is trapped in the fine fiber and in the oil/protein emulsion is released from the fine fiber and the emulsion inside the disc stock 910 and becomes "free oil," which travels inward to a small radius by density difference. The oil is then scooped by a skimmer 906 as a light phase discharge from the top of the centrifuge 900. The oil free (oil removed) heavy stream comes on outer edge of disc stock 909 then divided into two streams: a) one stream with heavier solid such as fiber, starch, and grit, which is discharged with a portion of liquid as a slurry through the open area of nozzle 911 (which is located on the outer edge of the bowl 912) as a nozzle discharge flow or underflow and b) the other stream with light solid (such as protein and fine germ particle) is discharged with a portion of liquid going through the space 913 between the bowl top 915 and the top disc 914 and is discharged as a heavy phase discharge from the side 916 in side of the top housing 922 of the centrifuge 900. The size of nozzle (nozzle open area) 911 is used to control liquid split ratio between the nozzle flow (underflow) and the heavy phase discharge.

Figure 4:
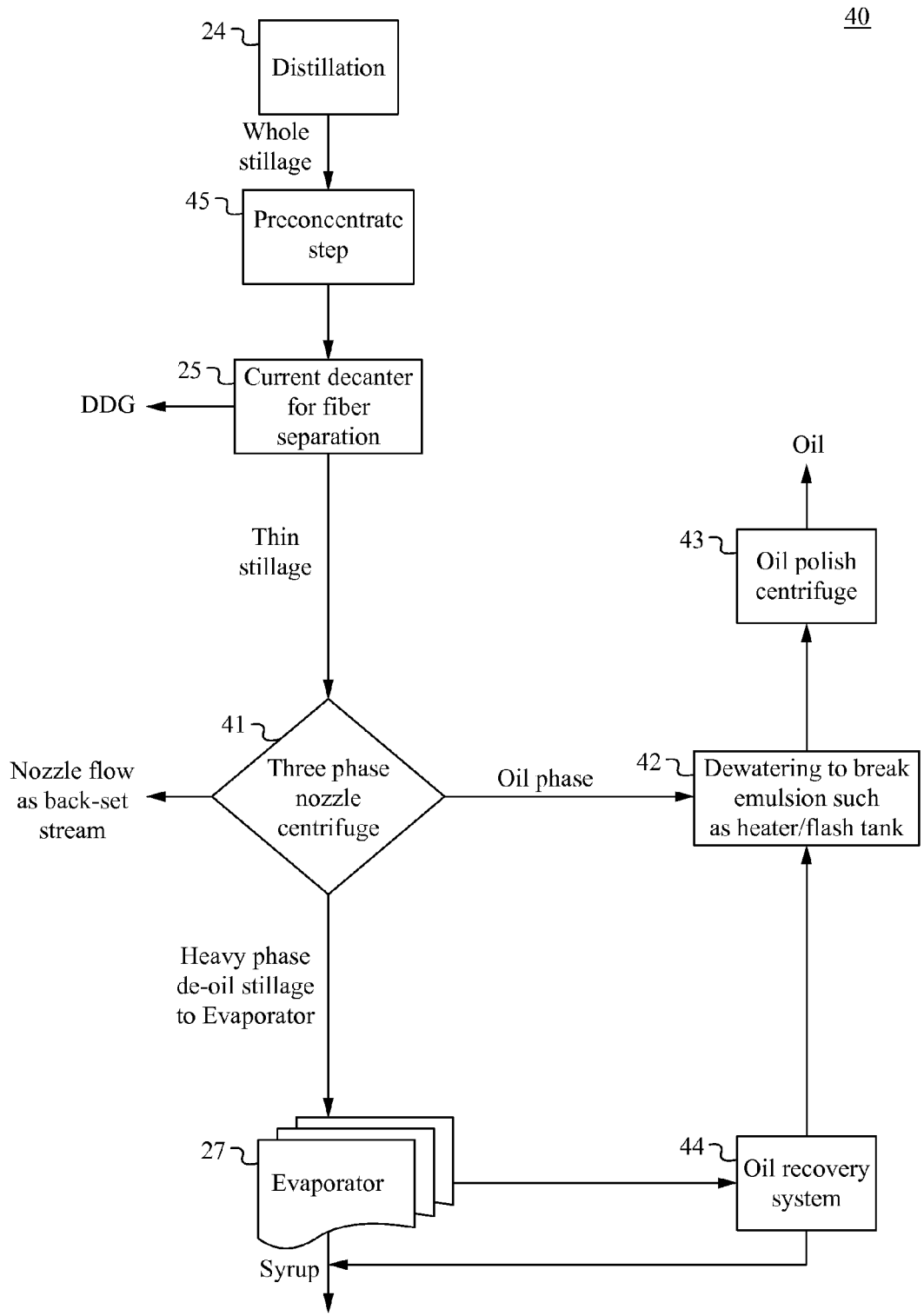
FIGS. 4, 4A, and 4B illustrate processes using two centrifuges in series for recovering oil from a whole stillage in a dry mill in accordance with some embodiments of the present invention.

FIG. 4 illustrates a process 40 using two centrifuges in series for recovering oil and protein from a whole stillage in a dry mill in accordance with some embodiments of the present invention. The process 40 is able to be operated in conjunction with the three-phase nozzle centrifuge 900 (FIG. 9) for skimming the oil/emulation from the thin stillage, then followed by using the oil polishing centrifuge (which is able to be a typical decanter or disc centrifuge) to recover and purify the oil from the oil/emulation stream.

Referring to FIG. 4, a whole stillage from a distilling step 24 (after a fermentating step that is not shown for simplicity) optionally goes to a pre-concentrating step 45 (pre-evaporated) before the whole stillage is sent to a fiber separating step 25. A decanter centrifuge or fiber centrifuge are able to be used at the fiber separating step 25 to separate the fiber (DDG) cake from liquid (thin stillage), which contains protein, oil, oil/protein emulsion, and fine fibers with bonded starch and trapped/absorbed oil. The thin stillage then goes to a three-phase nozzle centrifuge for a centrifuging step 41. At the centrifuging (a separation) step 41, the thin stillage is separated into three discharged streams including a) a light-phase discharge (an oil phase), which contains mainly oil and oil/protein emulsion and any solid having a density smaller than the density of liquid, such as fine germ particles and fine fiber trapped/absorbed oil, b) a heavy-phase discharge, which contains mainly protein in a slurry form and a small amount of oil/protein emulsion and fine germ particles, and c) the nozzle-flow (underflow), which contains mainly the oil-free-fine fibers with bonded starch and fine grits in a slurry form.

The light-phase discharge from the three-phase nozzle centrifuge at the separating step 41 goes to an emulsion breaking step 42 before the light-phase discharge is sent to an oil polishing step 43 using an oil-polishing-centrifuge to recover oil.

The emulsion breaking step 42 is able to be performed by typical methods that are used in the dry mill process for recovering oil at the back-end system, such as adding chemicals, adding alcohol, and heating to a high temperature. Alternatively in some embodiments of the present invention, the emulsion breaking is able to be performed by a dewatering step. The dewatering step is able to be combined to be used with a heat exchanger and/or a flash tank. The dewatering step (either under vacuum or not) is able to break the oil/protein emulsion by removing water. The dewatering step is able to be performed with a vacuum or negative pressure. The dewatering step is also able to break the germ oil cell wall inside the fine germ particles by drying the fine creamy germ pasty, such that the oil is able to be released.

After the emulsion breaking step 42, the wet agents, such as $Na_2CO_3$ or $Na_3PO_4$, are able to be optionally used to wet those dry solid before the dry solid are fed to an oil-polishing-centrifuge at the oil polishing step 43 to polish the oil stream and to produce pure oil. The oil-polishing-centrifuge is able to comprise a three-phase decanter or a disc type centrifuge. Alcohol is able to be optionally added to the solid with residual oil from the oil-polishing-centrifuge to extract the residual oil. The solid is able to be optionally recycled back to the front-end to recover more oil. With the steps mentioned above, the solid is able to contain less than 3% of oil in the dry solid. The oil yield using the methods and device disclosed herein is able to be around 0.4 to 0.6 lb/Bu.

The thin stillage normally contains only about 2 to 3% oil. A major portion of oil is either bonded with protein forming an oil/protein emulsion or trapped/absorbed in the fine fiber. The oil/solid mixture (oil/protein emulsion and oil/fiber) has a density about the same density as the liquid that contains the oil/solid mixture. It is very hard to recover the oil using a typical one-step centrifuge. In contrast, the two centrifuges (the three phase nozzle centrifuge at the step 41 and the oil-polishing-centrifuge at step 43), in accordance with some embodiments, are effective and efficient in recovering oil from the thin stillage. In the two centrifuges in series case, a high speed nozzle centrifuge (creating a high G-force) as the first centrifuge collects the oil/solid mixture as a light phase. A second centrifuge (oil-polishing-centrifuge) polishes oil and produce pure oil. The two centrifuges in series (e.g., steps 41 and 43; a two stage centrifuging process) are able to avoid the building up of the emulsion layer inside the centrifuges, so that the separation/isolation of the oil from the liquid phase is able to be effective.

Still referring to FIG. 4, the heavy phase discharge from the three phase nozzle centrifuging step 41 that contains mainly the protein and partially de-oiled germ particle is sent to an evaporator at a evaporating step 27 to be concentrated to around 35% DS as a syrup. In some embodiments, extra oil is able to be recovered from the syrup (with 20 to 40% DS solid) by sending the syrup to a back-end oil recovery system. In some embodiments, the recovery of the extra oil from the syrup is able to be performed using a back-end oil recovering system, such as the step 16 of FIG. 1 to FIG. 3A. The oil-removed syrup is able to be mixed with a decanter cake (DDG) from the fiber separating step 25 and sent to a DDGS dryer to produce DDGS.

The nozzle flow stream (underflow) from the three-phase nozzle centrifuging step 41 is able to be used as a back-set stream for the slurry tank (at the front-end) to be cooked with the ground corn flour.

The advantage aspects of the processes and devices disclosed herein include a) increasing the alcohol yield by about 0.5% (the nozzle flow stream contains most not-yet-converted starch (normally has about 5 to 7% starch), the not-yet-converted starch is able to be recycled back to the front-end as a back-set stream to be further liquefied to produce more alcohol) and b) the evaporator is able to produce a higher syrup concentration without fouling the evaporator (the heavy phase discharge contains less solid than the whole thin stillage (because more solid in the nozzle flow than in the heavy phase)). The % DS in the syrup is increased from 35 to 40%. This syrup stream contains 8 to 10% oil, which is able to be further recovered by a syrup de-oiling step 44 to recover more oil. An additional 0.1 lb./Bu oil yield is obtained with the syrup de-oiling step 44.

In the patent application (PCT/US12/30337; file on May 23, 2012; titled "DRY GRIND ETHANOL PRODUCTION PROCESS AND SYSTEM WITH FRONT END MILLING METHOD"), the fiber from a fiber separating step 25 at a dry mill plant contains germ particles (about half of the germ in corn), which can result in as high as 9% of oil trapped in the fiber not been released. The above patent application is incorporated by reference in its entirety for all purposes.

Figure 3:
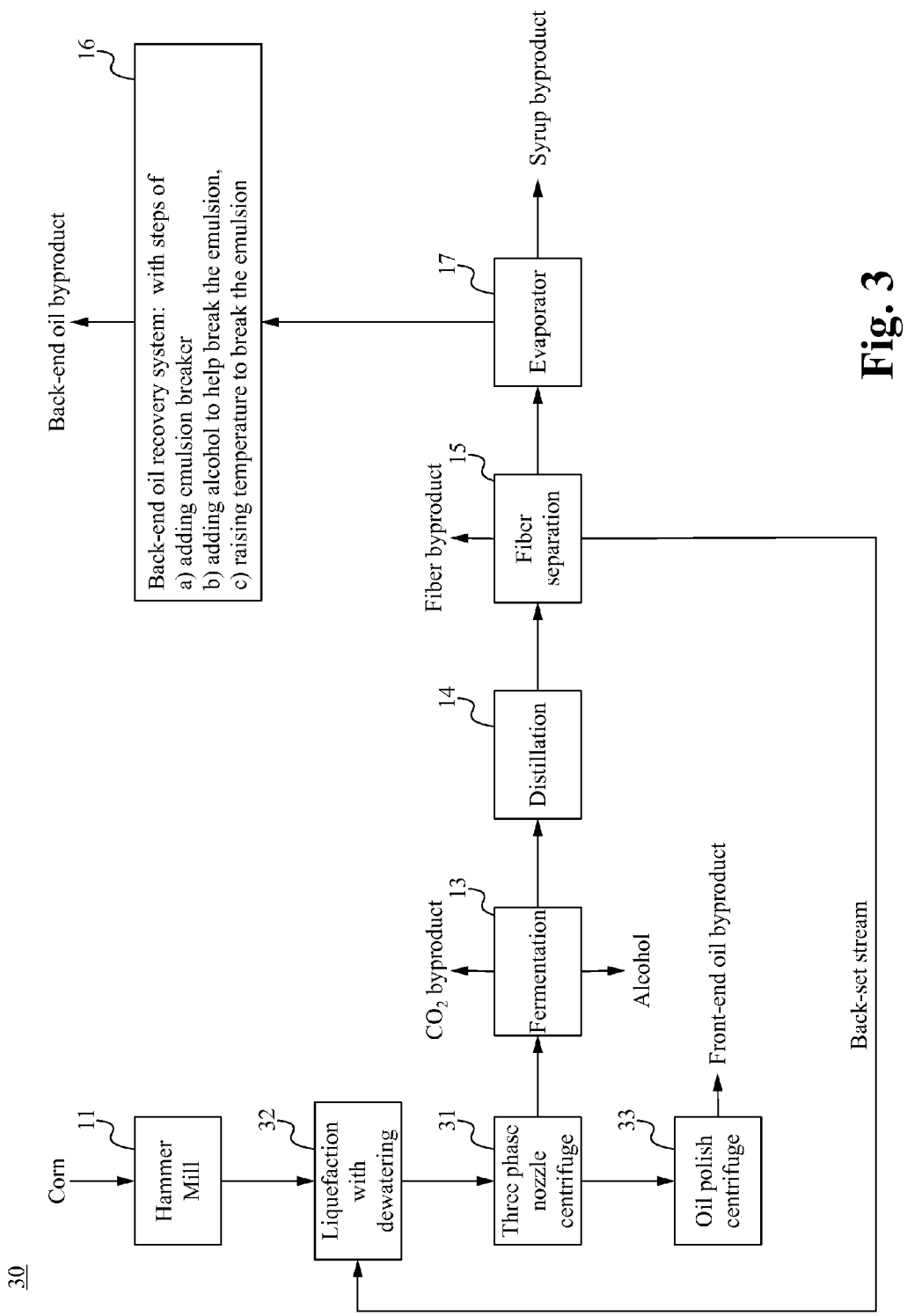
FIG. 3 is a typical dry mill process having a front-end dewatering mill system and a front-end oil recovery system.

In the above process (as shown in FIG. 3), a front-end dewatering milling step 32 at the front-end (before fermenting step) is used. The front-end dewatering milling step 32 requires three milling stages to reduce the oil content from 9% to 3%, because the germ particles in the front-end are much harder. Therefore, the germ particles at the front-end are more difficult to be broken up for the oil to be released. The process that uses three milling stages consumes a lot of energy. (In the above process, if one milling stage is used, the oil content is able to be reduced to around 7%. When two milling stages are used in series, the oil content is able to be reduced to 5%. When three milling stages are used in series, the oil content is able to be decreased to 3%.)

Figure 4A:
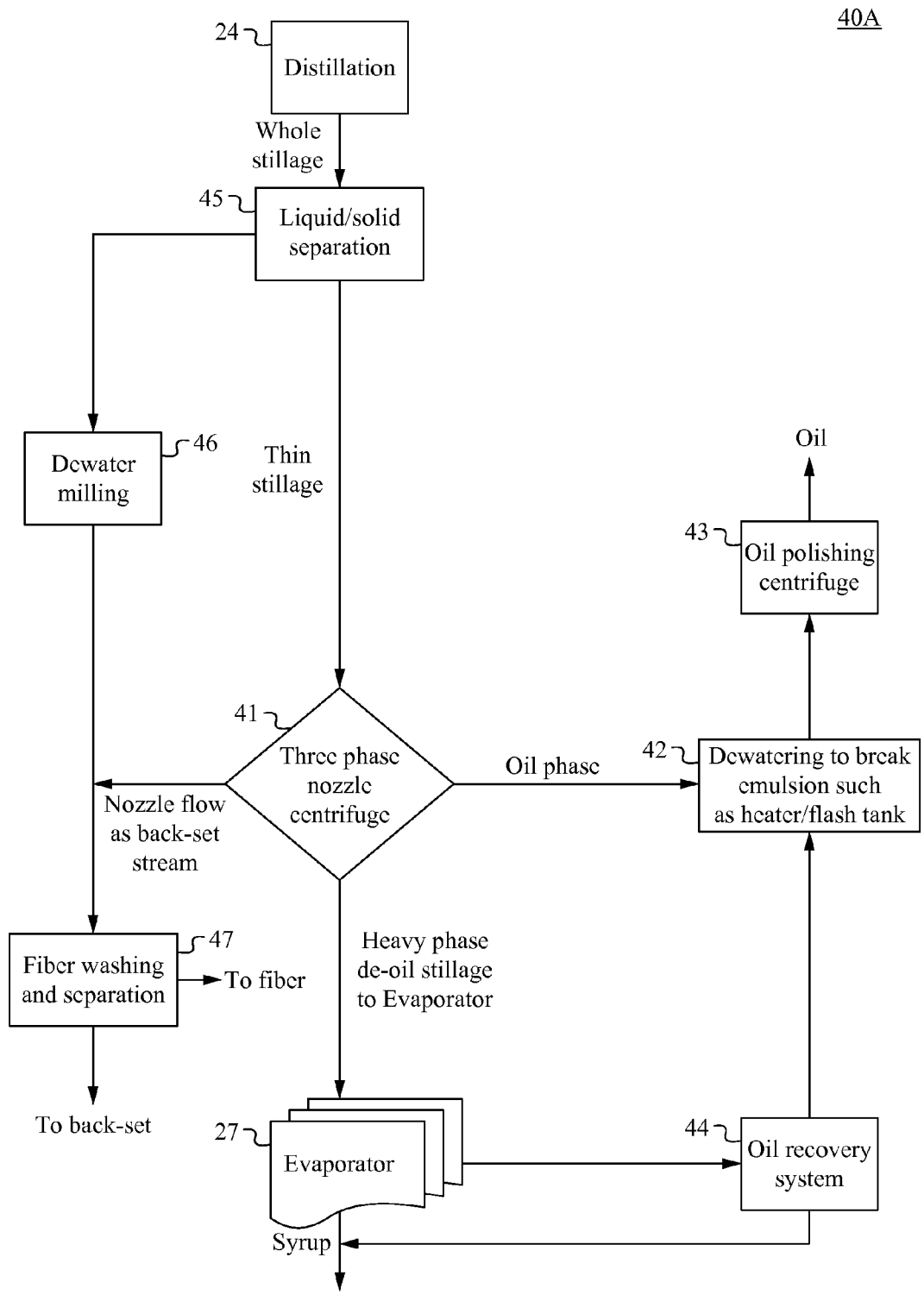

Accordingly, a more advantageous back-end milling process with only one milling stage is disclosed herein. FIG. 4A illustrates a process 40A having a back-end dewatering milling step for recovering oil from a whole stillage in a dry mill process in accordance with some embodiments of the present invention. The germ particles in the whole stillage (in the back-end that are after the fermenting and distilling stages) are much softer, so the germ particles are easier to be broken up and the oil is able to be released more easily.

Additionally in some embodiments, a pH value of the solution is adjusted to 7 to 9 before or during the dewater milling step 46, which makes the germ cell wall breaking and oil releasing from the germ cells become much easier. With only one dewater milling stage at the back-end, the oil content in the fiber is still able to be decreased from 9% to 3%.

More details of the process 40A of FIG. 4A are described in the following. The process 40A of FIG. 4A is similar to the process 40 of FIG. 4. The process 40A further includes a dewater milling step 46 and a fiber washing separating step 47. In the process 40A of FIG. 4A, the whole stillage is sent to a liquid/solid separating step 45 after the distilling step 24 at the back-end process. The liquid portion (thin stillage) of the liquid/solid separating step 45 goes through a two-stage centrifuge separating stage in series (e.g., the three-phase disc centrifuge step 41 follow by oil polishing centrifuging step 43) for oil recovery. The solid portion (fiber) that contains germ particles goes through a dewater milling step 46, so that the germ particles are able to be broken up to release oil.

Next at a fiber washing and separating step 47, the nozzle flow from the three phase nozzle centrifuging step 41 is used as washing water to wash and separate fiber from the oil and protein stream. The washing liquid is sent to the front-end as back-set water. The fiber through the washing and separating step 47 contains less than 10% of protein and less than 3% of oil. The fiber with low protein and oil content is an idea feed stock for a cellulose to alcohol process.

Figure 4B:
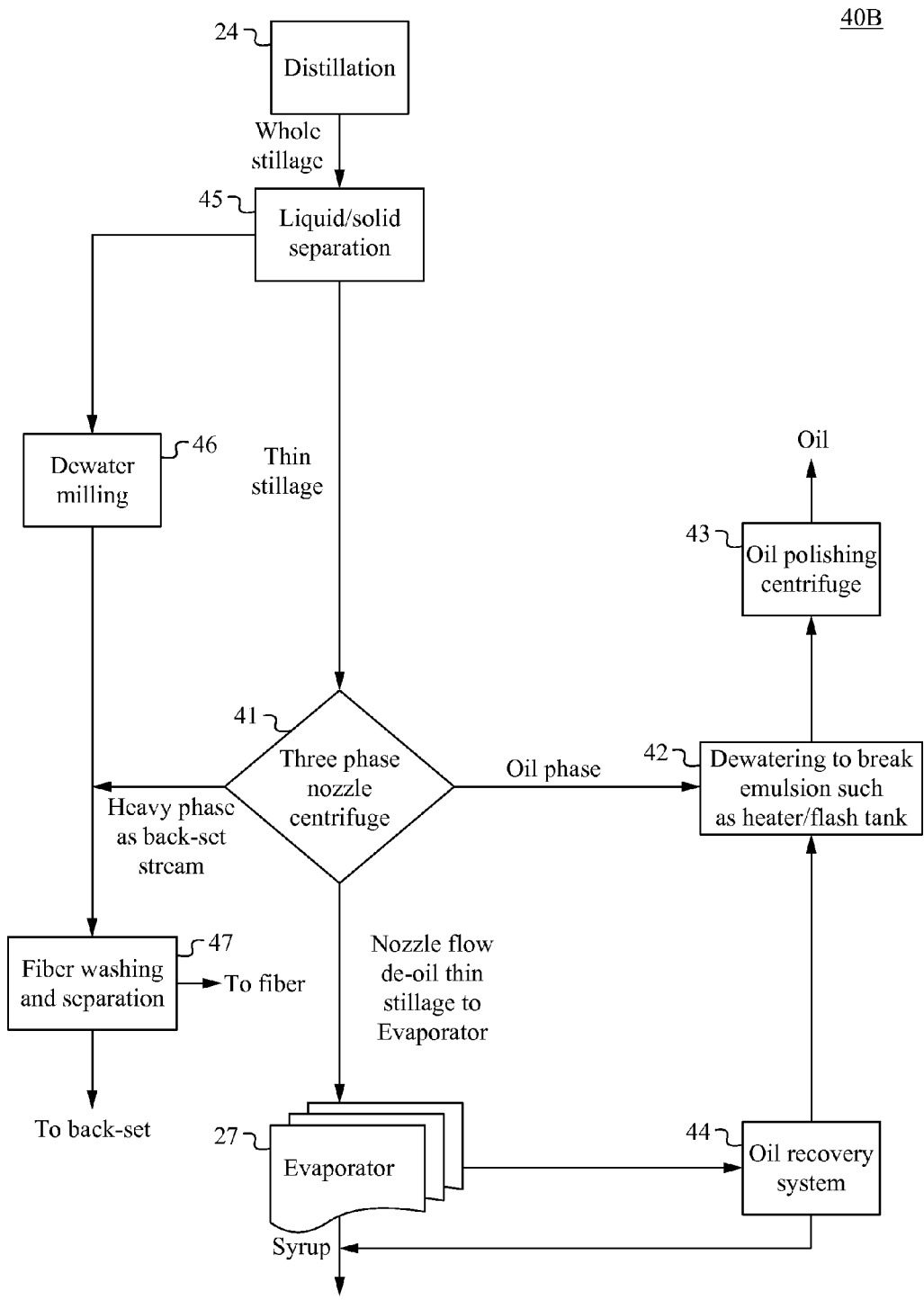

FIG. 4B illustrates a back-end process 40B similar to the process 40A of FIG. 4A. In the fiber washing and separating step 47 of the process 40B, the washing water is coming from a heavy phase discharge stream of the three-phase nozzle centrifuge step 41.

Figure 5:
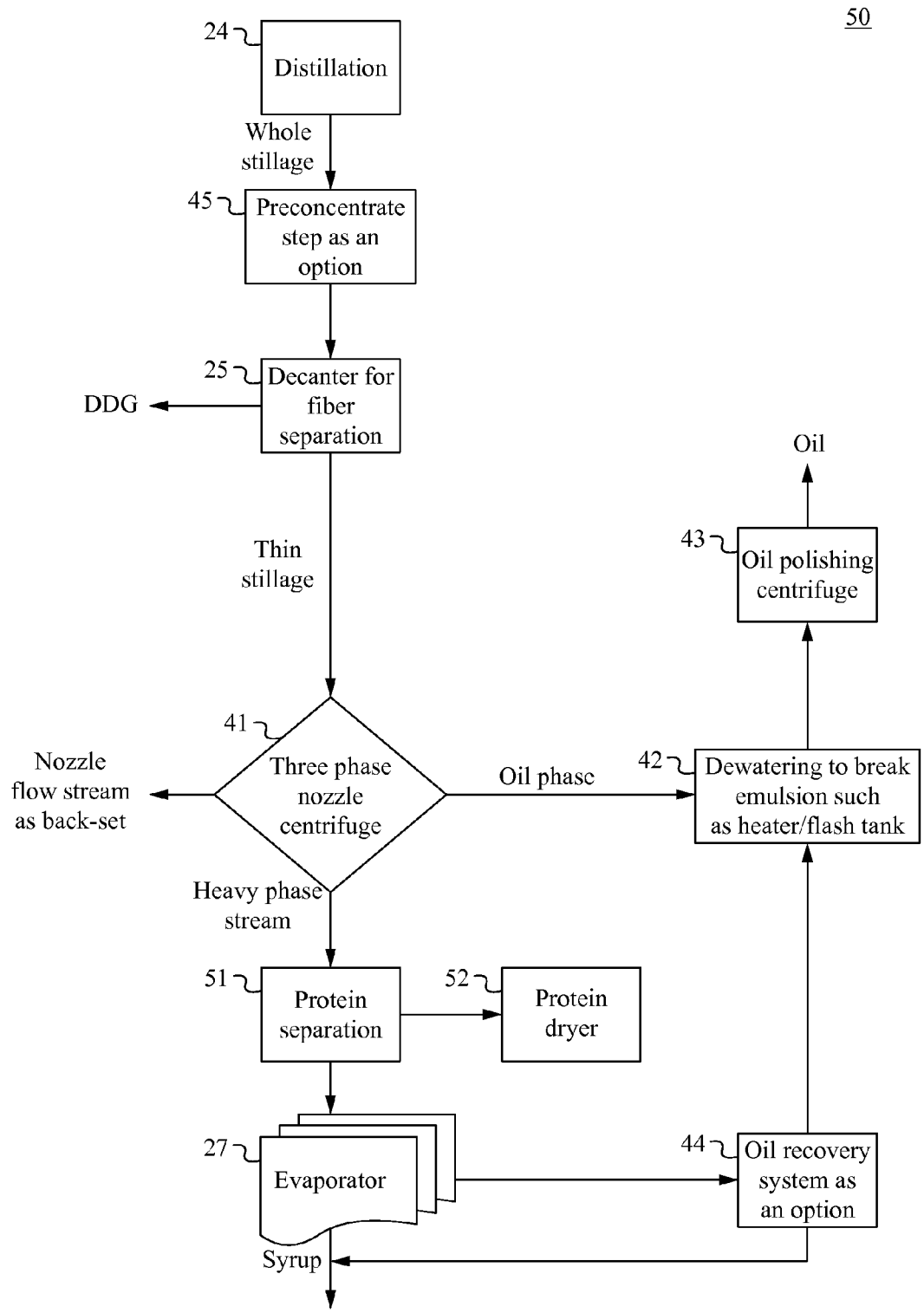
FIGS. 5 and 5A illustrate two-centrifuge in series processes for recovering oil and protein from a whole stillage in a dry mill in accordance with some embodiments of the present invention.

FIG. 5 illustrates another two-centrifuge in series process 50 for recovering oil and protein from a whole stillage in a dry mill in accordance with some embodiments of the present invention. The process 50 is similar to the process 40 of FIG. 4. Process 50 further includes a protein recovery system (including protein separating step 51 and a protein drying step 52) to recover protein and produce protein meal. Protein is the main constituent in the heavy phase discharge from the three-phase nozzle centrifuge at the centrifuging step 41.

Accordingly, the heavy phase from three-phase nozzle centrifuge at the centrifuging step 41 is sent to the protein separating step 51 to recover proteins. Decanters or other types of liquid/solid separation equipments are able to be used at the protein separation step 51. The cake (protein) from the decanter is sent to a protein dryer at the protein drying step 52 to produce protein meal. In some embodiments, the protein meal contains 50% protein, which is able to be used as chicken and pig feed. The protein meal has a higher value than DDGS. The overflow from the protein separating step 51 is mainly oil and solid-free liquid, which are able to be fed to an evaporator at an evaporating step 27. At the evaporating step 27, the overflow is able to be concentrated to contain a syrup with DS as high as 80% DS. This syrup contains germ particles with oil (as high as 10%) in the syrup. The oil recovering step 44 is able to recover additional oil from the syrup. With the oil recovering step 44, the oil yield is able to increase 0.1 lb./Bu. The concentrated oil-removed syrup is able to be mixed with the cake (DDG) from a fiber separation step 25 to produce DDGS. The DDGS production described herein is able to use less gas at the DDGS dryer comparing to the typical method because of the higher concentration of the syrup. The high percentage of the DS in the syrup contains more than 14% potassium and more than 10% phosphate, which are able to be used as organic plant food.

Figure 5A:
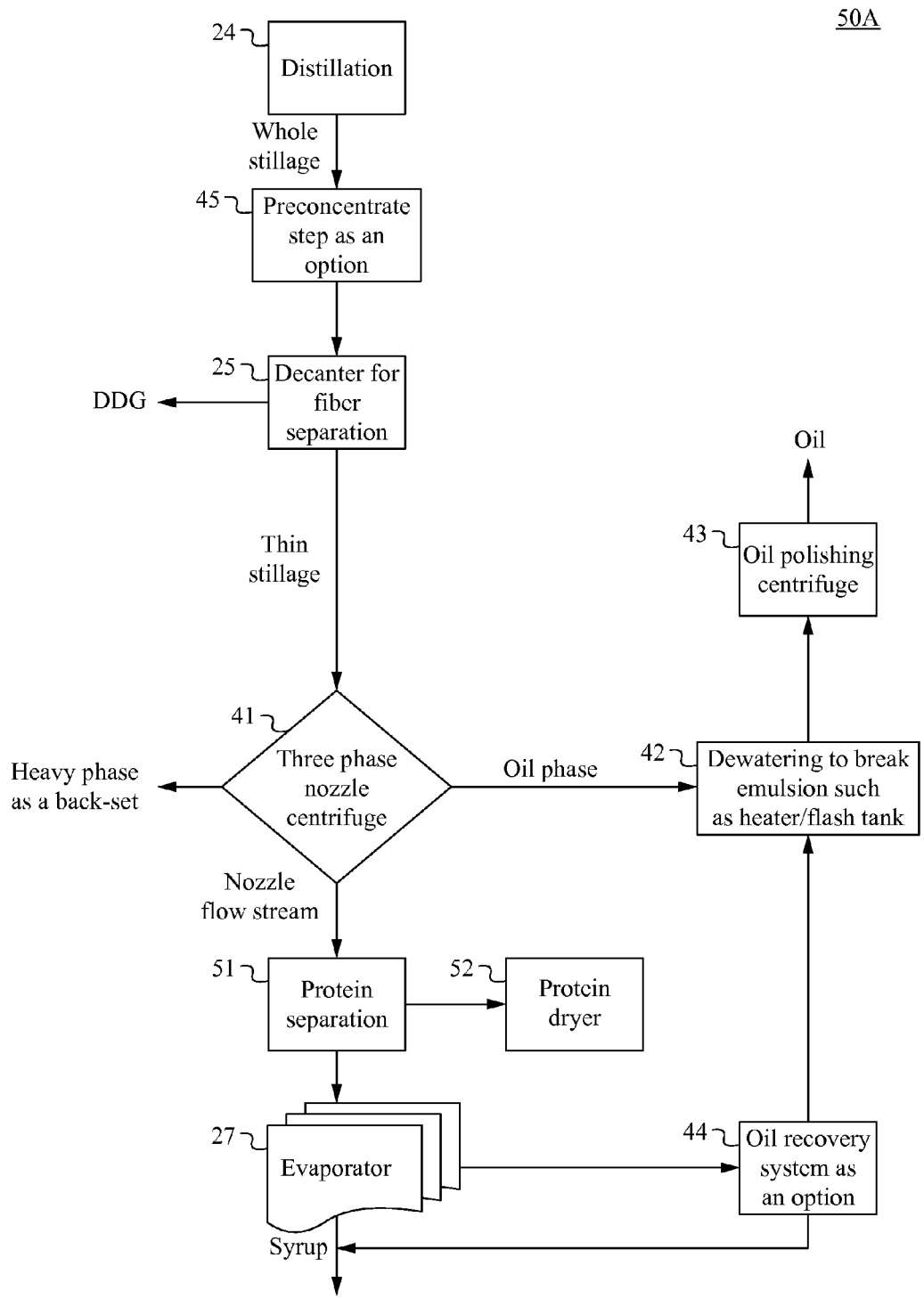

FIG. 5A illustrates another two centrifuges in series process 50A for oil and protein recovering in accordance with some embodiments of the present invention. The process 50A is a variation of the process 50. The process 50A is able to produce a high yield of oil. Most of the steps in the process 50A are similar to the steps in the process 50. In the process 50A, the heavy phase discharge from the three-phase nozzle centrifuge at the centrifuging step 41 is sent/recycled back to the front-end to recover more oil. The nozzle (underflow) discharge stream is sent to a protein separation step 51.

The process 50 of FIG. 5 produces a higher alcohol yield and a protein meal with higher protein content, because the fiber with bonded starch and grits are recycled back to the front-end. The process 50 of FIG. 5 produces about 3.5 lb./Bu protein and 0.9 lb./Bu oil with a 0.5% alcohol yield increases. The process 50A of FIG. 5A produces a higher oil yield (1 lb./Bu) and a higher protein yield (4.5 lb./Bu), because the fine germ particle is recycle back to the front-end to release more oil.

Figure 10:
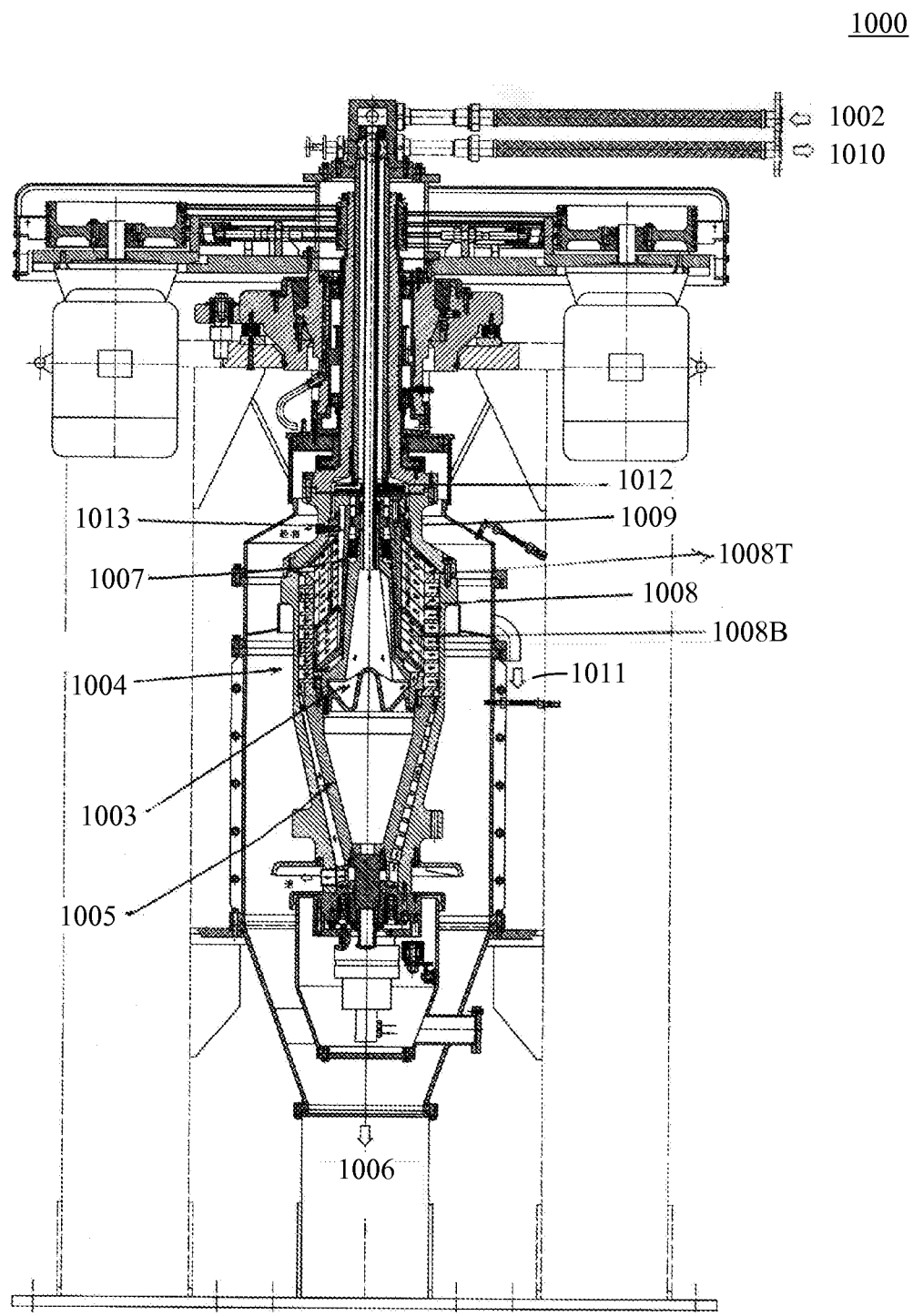
FIG. 10 illustrates a three-phase disc decanter in accordance with some embodiments of the present invention.

FIG. 10 illustrates a three-phase disc decanter 1000 in accordance with some embodiments of the present invention. The three-phase disc decanter 1000 comprises/combines both the functions and structures of the three-phase nozzle centrifuge (Step 41) and the decanter centrifuge (Step 51) of FIGS. 5 and 5A. As such, the three-phase disc decanter 1000 is able to recover oil and protein at the same time with the single machine/device.

As shown in the FIG. 10, a feed is coming from the top 1002 of the three-phase disc decanter 1000 into a center section of bowl 1003. The solid of the feed is settled to the wall of the bowl 1004 and is discharged by a screw conveyor 1005 to a solid end (on the bottom of the machine) 1006. The oil phase of the feed stays close to the center 1007 of the three-phase disc decanter 1000. The major portion of the liquid and solid in the feed enters to a disc stock 1008. The fine solid (mainly protein) is settle to the outer edge of the disc stock 1008, which is then discharged to the solid end 1006 though the conveyer 1005. The clean liquid with a small amount of light solid, such as fine germ particles and/or emulsion comes out through the space between the bowl top 1009 and the top disc 1015. The clean liquid is discharged though a pare disc 1012 as a heavy phase discharge 1010 from top of machine. Oil is discharged through nozzle 1013 as light phase 1011 from the side of the three-phase disc decanter 1000. Since the three phase disc decanter 1000 has a much higher disc height/disc diameter ratio (larger than 1) comparing with the typical disc centrifuge, which has only about 0.7 of disc height/disc diameter ratio, the disc stock 1008 is able to be divided into two sections. The two sections are arranged one on top of the other. The feed enters into a first set of disc stock in the bottom 1008 B, then the feed goes to a second set of disc stock 1008T (at the top). Accordingly, the three-phase disc decanter 1000 is able to perform the functions of the both three-phase nozzle centrifuge (Step 41) and the decanter centrifuge (Step 51) in series as described in the FIGS. 5 and 5A.

The two disc stock in series inside the three phase disc decanter 1000 is able to include various disc stock designs with various functions to meet the needs of various applications. In some embodiments, the disc stock design includes clarifier disc stock design, or concentrator disc stock, purifier disc stock, or a combination thereof. The clarifier disc stock design comprises a feed hole at the outer edge of the disc. The concentrator disc stock design comprises a feed hole at inside edge of the disc. The purifier disc stock comprises a feed hole in the middle of the disc stock.

Figure 10A:
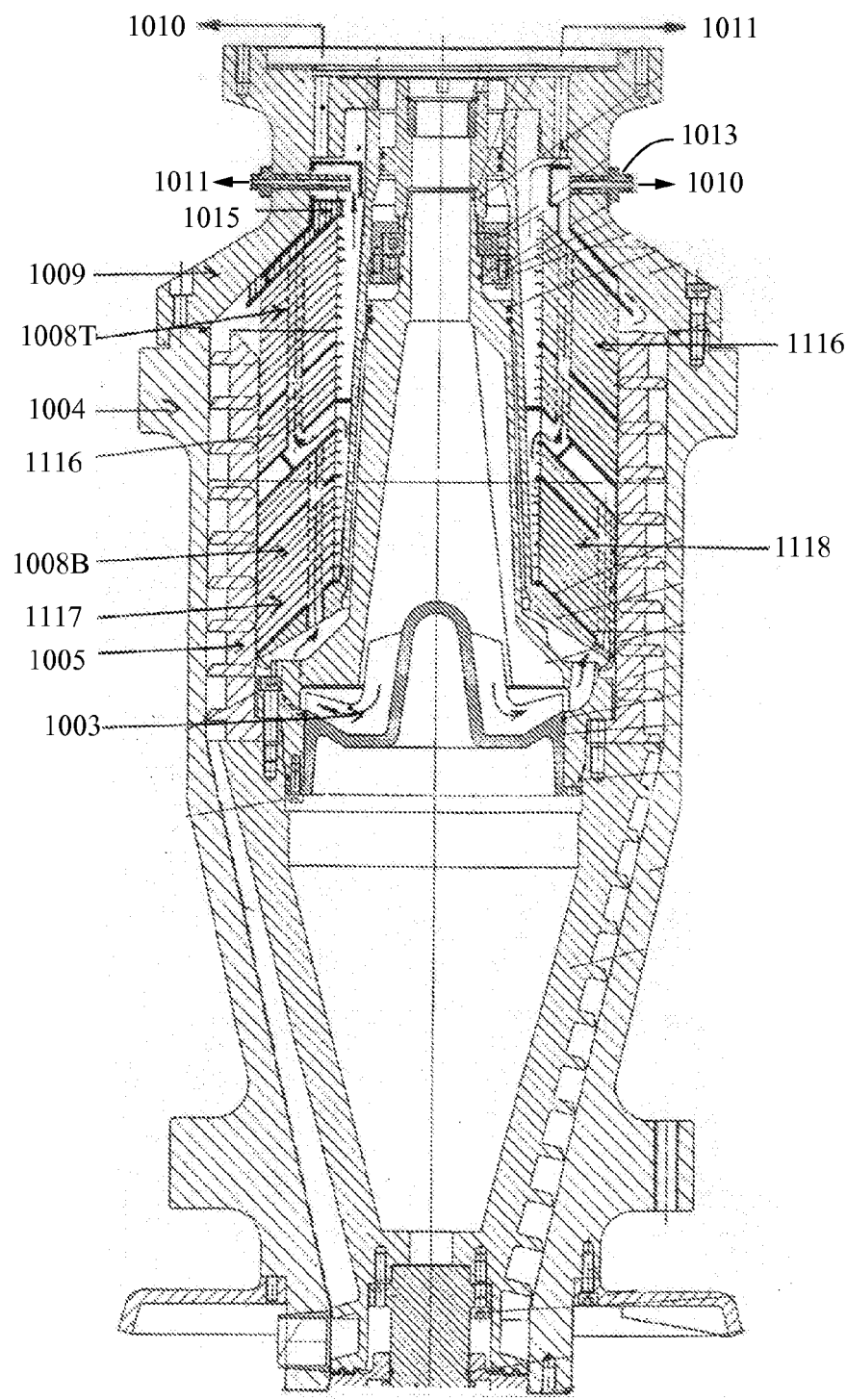
FIG. 10A illustrates another disc decanter in accordance with some embodiments of the present invention.

FIG. 10A illustrates another disc decanter 1100 in accordance with some embodiments of the present invention. The numbers for labeling the components that are used in the FIG. 10 are also applicable in the FIG. 10A. For example, a center section of bowl 1003 in FIG. 10 is able to be the sample component of a center section of bowl 1003 in FIG. 10A. The disc decanter 1100 comprise a clarifier disc stock 1117 followed by a purifier disc stock 1116 on the right side and a concentrate disc stock 1118 followed by a purifier disc stock 1116 on the left side. The disc decanter 1100 is able to generate a 8000 G force that is much greater than the typical decanter, which can only generate a force of 3000 G. The disc decanter 1100 is superior than a typical decanter, because the disc decanter 1100 is able to produce proteins with lower % of oil (less than 2% oil in the protein meal) and a cake that is drier than the products produced by the typical decanters. The disc decanter 1100 is able to produce a cake with about 30% of DS comparing to a cake with only 25% of DS by a typical decanter. The oil yield of the disc decanter 1100 increases about 0.1 lb./Bu comparing with the oil yield of a typical decanter.

Figure 5B:
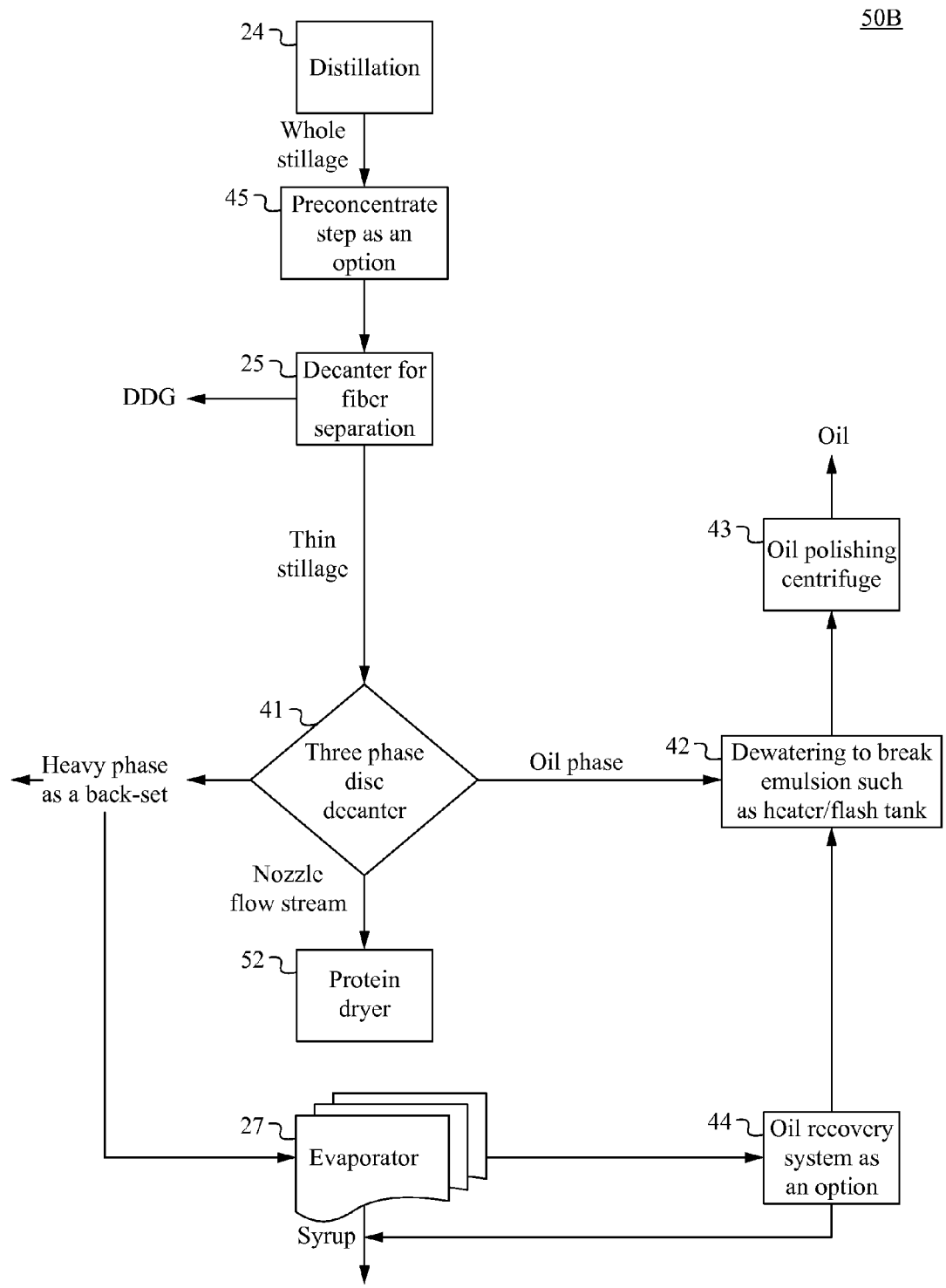
FIG. 5B illustrates a process having the three-phase disc decanter and/or the disc decanter in accordance with some embodiments of the present invention.

FIG. 5B is a flow chart illustrating a process 50B having the three-phase disc decanter 1000 (FIG. 10) and/or the disc decanter 1100 (FIG. 10A) in accordance with some embodiments of the present invention. In some embodiments, the process 50B comprises a separating step 53 using a three-phase disc decanter (e.g., the three phase disc decanter 1000 (FIG. 10) and/or the disc decanter 1100 (FIG. 10A)) that is able to replace the three-phase nozzle centrifuge step 41 follow by a protein separating step 51 of FIGS. 5 and 5A.

The back-end oil recovering step 44 is able to be used to increase the oil yield about 0.1 lb./Bu and recover protein at the same time. The three phase disc decanter 1000 (FIG. 10) and/or the disc decanter 1100 (FIG. 10A) is able to be applied to any of the processes (e.g., FIGS. 4-8) disclosed herein.

Figure 6:
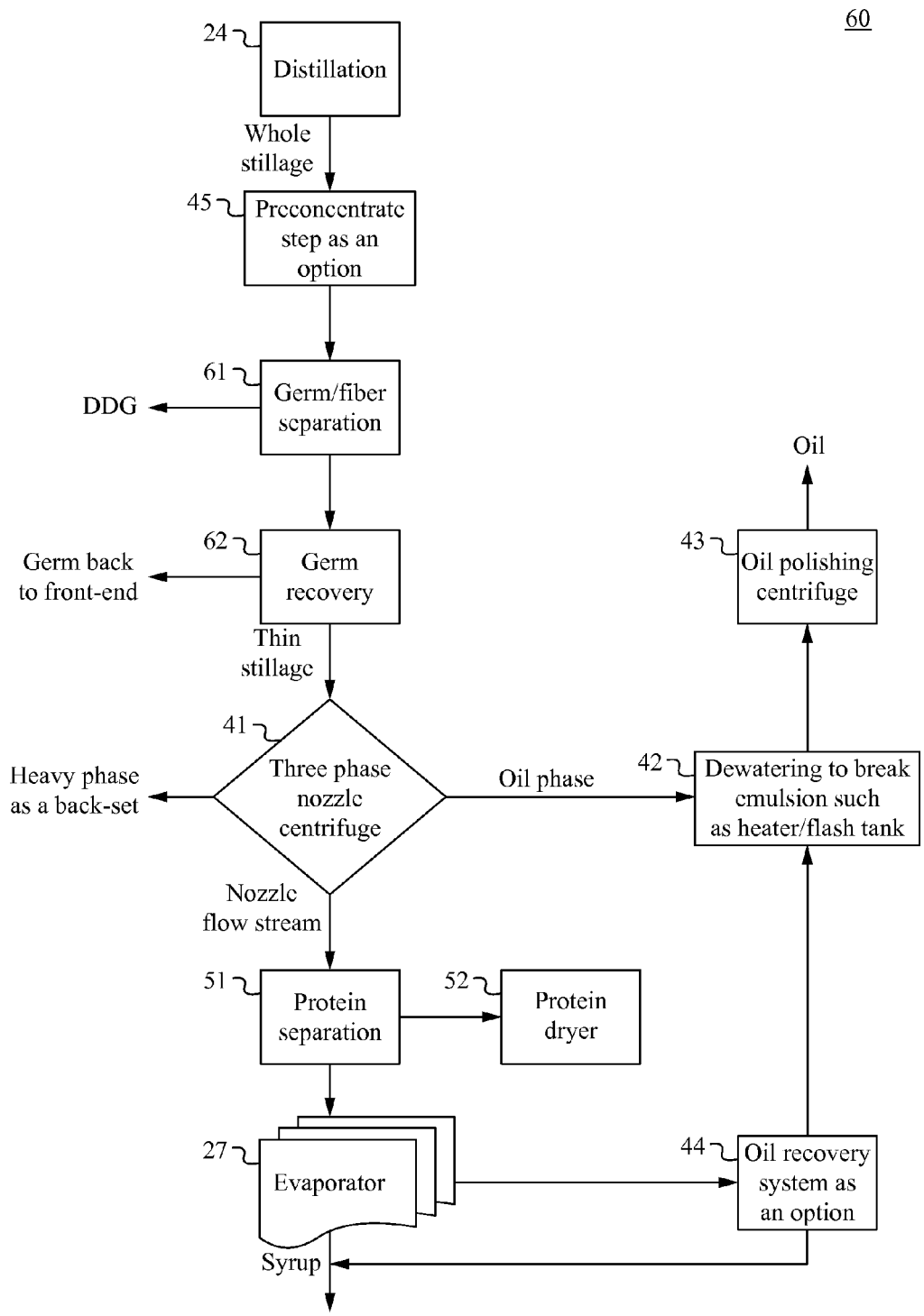
FIG. 6 illustrates a two-centrifuge in series process for oil and protein recovery in a dry mill process in accordance with some embodiments of the present invention.

FIG. 6 illustrates a two-centrifuge in series process 60 for oil and protein recovery in a dry mill process in accordance with some embodiments of the present invention. The process 60 comprises a germ/fiber separating 61 and a germ recovering step 62, which are steps allowing more oil to be recovered. In a whole dry mill process, only about half of the germs in the corns are broken out and release oil. Other half of the germs still maintain in a germ form with varied particle sizes. The germs that are grinded to small sizes release some of the oil during a fermenting step. However, the larger particle sizes germs still contain 30 to 50% of oil in the germ. Accordingly, the germ/fiber separating step 61 and the germ recovering step 62 are able to help to release more oil from the germs by separating and recovering germs from the fiber.

Still referring to the process 60, the germ/fiber separating step 61 is able to use a germ cyclone or decanter with a classification design or a combination of a germ cyclone followed by a fiber dewatering device such as decanter or fiber centrifuge to separate germs from the fibers by density differences (germs have a density around 1 gram/ml and fiber has a density of 1.2 gram/ml). The germ recovering step 62 is able to comprise a paddle screen or any other types of liquid/solid separating devices, such as a pressure screen. The germs that are recovered at the back-end are sent back to the front-end (i.e., before a fermenting step which is prior to the distillation step 24 in all Figs.) The germ/fiber separating step 61 and the germ recovering step 62 are able to comprise a dewatering mill system, which is described in a U.S. Provisional Patent Application 61/638,455, filed on Apr. 25, 2012, entitled "SYSTEM FOR AND METHOD OF SEPARATING GERM FROM GRAINS USED FOR ALCOHOL PRODUCTION," which is incorporate by reference in its entirety for all purposes.

The recovered germs go though the dewatering mill step one more time to be broken up and release more oil. The germ/fiber separating step 61 and germ recovering step 62 recover about 40 to 50% germs in the whole stillage and increase the oil yield about 1.1 lb./Bu. A pre-concentrating step 45 is also able to increase a germ/oil yield, because the density of liquid increases that helps to float the germs and separated the germs from the fiber in the germ/fiber separating step 61.

Figure 7:
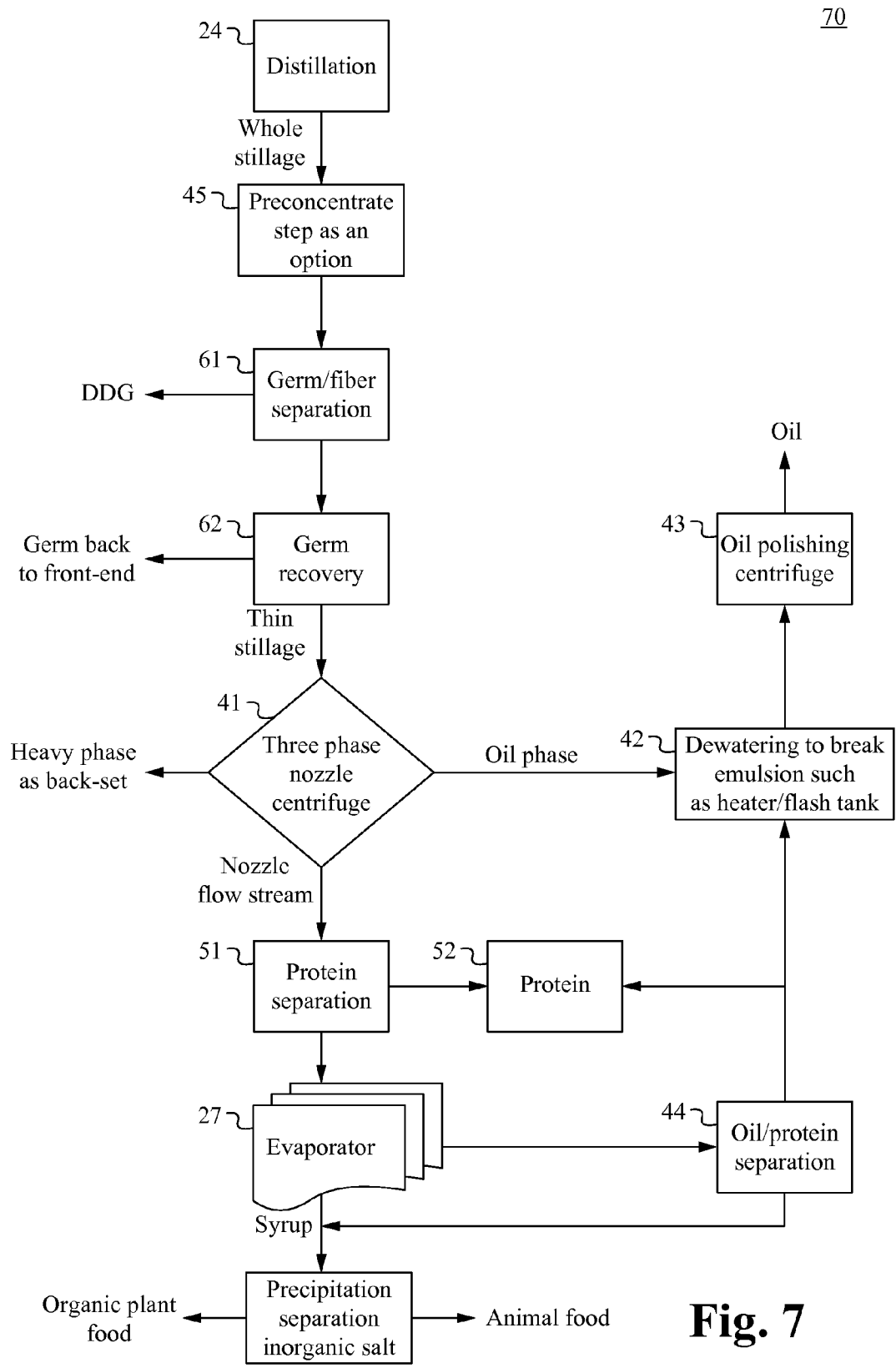
FIG. 7 illustrates a two-centrifuge in series process for recovering oil, protein, and germs in accordance with some embodiments of the present invention.

FIG. 7 illustrates a two-centrifuge in series process 70 for recovering oil, protein, and germs in accordance with some embodiments of the present invention. The process 70 is similar to the process 60 of FIG. 6. The process 70 comprises a oil/protein separating step 71 having a high G-force disc decanter, which is ideal for separating protein from syrup from the evaporating step 27. As described in the process 60, the germs are recycled back to the front-end at the germ recovering step 62. The germs that are de-oiled comprise high percentage of protein, which is fit for use as an animal feed. However, the particle sizes of the germ proteins are too fine so it is hard to be recovered from the syrup solution. Thus, the high G force disc decanter of the process 70 is an ideal device to separate the germ protein from the syrup.

The light phase discharge from disc decanter at the step 71 of the system 70 is sent to an emulsion breaking step 42 and followed by an oil polishing step 43 to recover oil. Alternatively, the light phase discharge from disc decanter at the step 71 is sent back to a front-end step and recovers oil in the front-end, which is able to be performed before and/or after the emulsion breaking step 42. Using the disc decanter at the step 71 of the process 70, the protein yield increases from 3.5 lb./Bu to 5 lb./Bu. The oil yield is around 1.2 lb./Bu by using the process 70.

At the evaporating step 27, the de-oil and de-protein syrup from the evaporator can be further separated into two portions. One portion is an organic compound rich portion, which is mainly the residue of sugar/starch from the fermentation and non-alcoholic by-products (such as citric acid, and glycerol etc). The other portion is an inorganic compound rich portion containing salts, coming mainly from the mineral salt inside the corn kennel. The inorganic compound rich portion contains high amount of potassium and phosphate, such that it can be used as an organic plant food. The separation of the de-oiled and de-protein syrup into two streams/portions can be achieved by first concentrating the syrup to 50 to 80% DS (optionally holding on low temperature to precipitate the inorganic salt), and then using any solid/liquid separation device, such as decanter centrifuge, to recover the inorganic salt, which can be used as a plant food. The liquid that mainly contains the organic compounds can be sent to a DDGS dryer to dry the liquid such that the resultant product can be used as an animal food.

Figure 8:
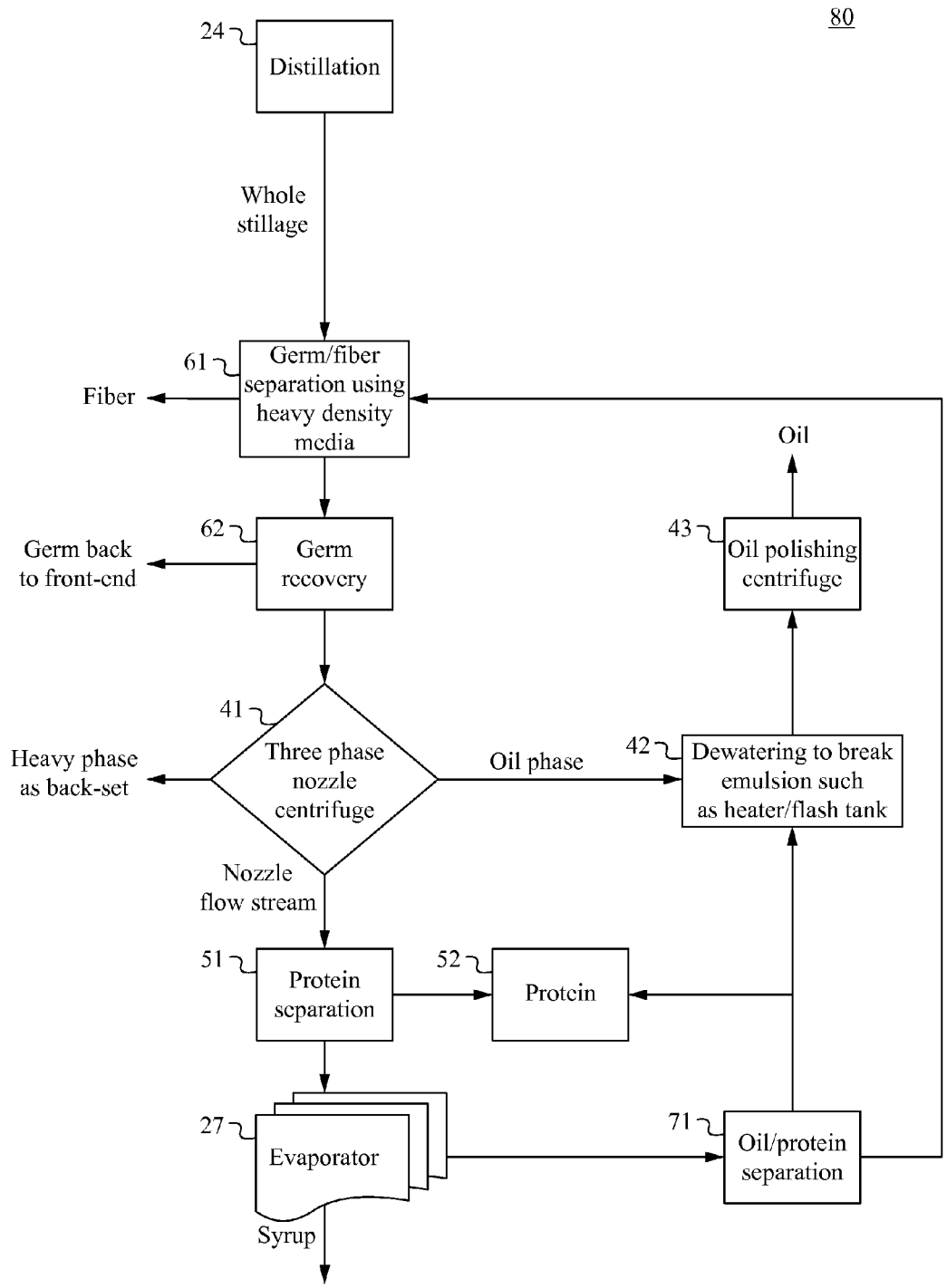
FIG. 8 illustrates a two-centrifuge in series process for recovering oil, protein, and germs in accordance with some embodiments of the present invention.
Figure 9:
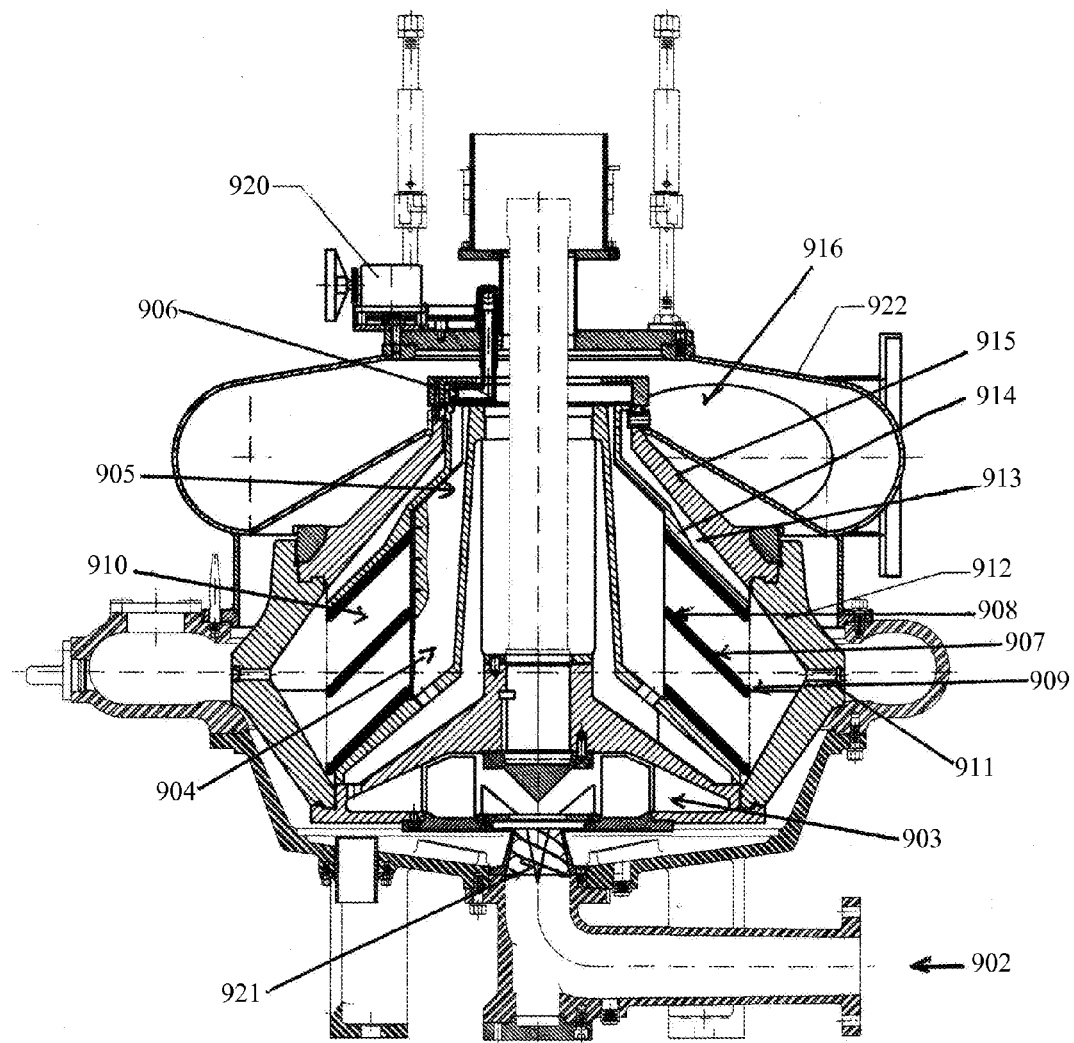
FIG. 9 is a cross-sectional view of a three-phase nozzle centrifuge in accordance with some embodiments of the present invention.

FIG. 8 illustrates a two-centrifuge in series process 80 for recovering oil, protein, and germs in accordance with some embodiments of the present invention. The process 80 is similar to the process 70 of FIG. 7. The process 80 is able to increase the yields of oil and protein further by recovering more germs from the whole stillage, which is achieved by recycling a portion of the concentrated syrup at the oil/protein separating step 71 back to the whole stillage at the step 61 to increase the density (e.g., to around 1.05 to 1.1 gram/ml) of the liquid (as a heavy liquid media) in the whole stillage such that more germs are able to be floated out. The germ yield is able to be increased to 70 to 80% by using the process 80. The oil yield using the system 80 is around 1.3 lb./Bu and protein yield is 6 lb./Bu.

Figure 3A:
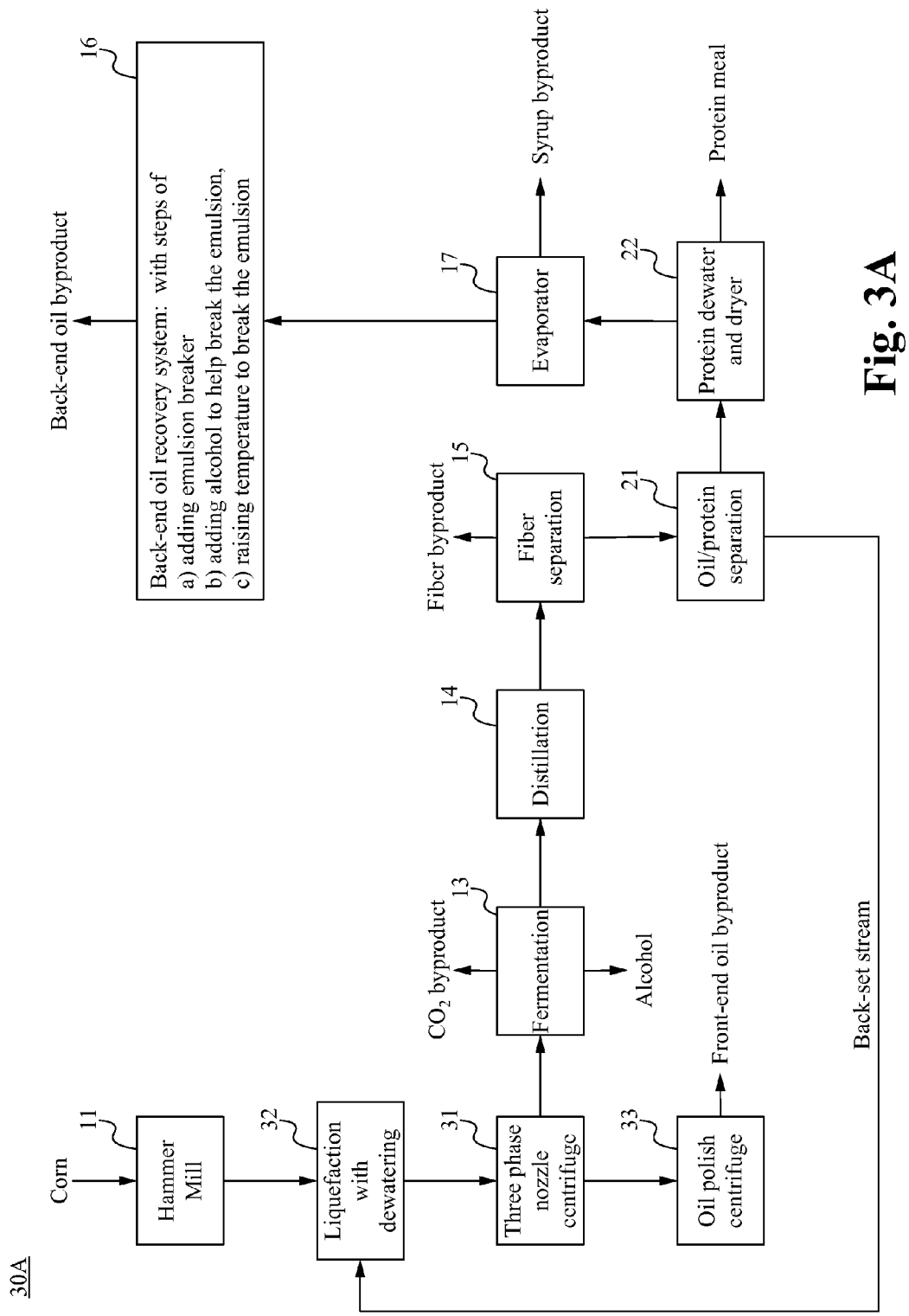
FIG. 3A is a typical dry mill process having a front-end dewatering mill system, a front-end oil recovery system, and a back-end protein recovery system.

The two centrifuges in series, a three-phase nozzle centrifuging step 41 and oil polishing centrifuging step 43 at the back-end describe above (from FIG. 4 to FIG. 8) are able to recover more oil from the thin stillage, which are different from the front-end oil system (a three-phase nozzle centrifuging step 31 followed by an oil polishing centrifuging step 33) and back-end single oil recovering system (single centrifuge step) in FIG. 3 and FIG. 3A. The devices disclosed herein are able to be combined and/or arranged in series to improve the product yields and results. For example, the front-end oil recovering system can combine with the back-end devices and methods disclosed herein. For example, the oil polishing centrifuging step 33 in the front-end system of FIG. 3 can be combined with an oil polishing centrifuging step 43 at the back-end of FIG. 4 to form a single unit machine, such that equipment costs are able to be reduced.

The patent application PCT/US09/45163; filed on May 26, 2009; titled "METHODS FOR PRODUCING A HIGH PROTEIN CORN MEAL FROM A WHOLE STILLAGE BYPRODUCT AND SYSTEM THEREFORE," is incorporate by reference in its entirety for all purposes. Further, the patent application PCT/US12/30337; file on May 23, 2012; titled "DRY GRIND ETHANOL PRODUCTION PROCESS AND SYSTEM WITH FRONT END MILLING METHOD," is incorporate by reference in its entirety for all purposes.

The processes and devices are able to be utilized in recovering oil and proteins from a corn based stillage. The process is able to be operated according to the sequences described in the figures or in any other sequences to improve the yields. The processes and devices are advantageous in many aspects including using two centrifuges in series and/or a dual function centrifuge to be more efficiently and effectively separate oil from the emulsions.

Although various systems and methods described herein use corn as an example. Any other types of grains, such as, wheat, barley, sorghum, rye, rice, and oats can be used. It is also contemplated that any byproduct, such as fiber protein from the current corn wet mill processes or germ fractions and fiber fractions from current dry fraction processes can be used. The process disclosed herein includes liquefying the starch in grain to a sugar solution. Next, oil, protein, and fiber are separated from the sugar solution. In some embodiments, the sugar solution is used to manufacture butanol, citric acid, lactic acid, and lysine.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A back-end two centrifuges dry mill system comprising a fermenter, a three-phase disc decanter and an oil polishing centrifuge, wherein the three-phase disc decanter and the oil polishing centrifuge are after the fermenter, wherein the three-phase disc decanter has a disc height/disc diameter ratio greater than 1, and wherein the three-phase disc decanter comprises two different disc stocks, and wherein the three-phase disc decanter comprises a three phase nozzle centrifuge and a decanter.

2. The system of claim 1, further comprising an emulsion breaking container is fluidly coupled with the three-phase disc decanter.

3. The system of claim 2, wherein the oil polishing centrifuge is fluidly coupled with the emulsion breaking container.

4. The system of claim 1, further comprising a fiber separation decanter is coupled with the fermenter and the three-phase disc decanter, wherein the fiber separation decanter located after the fermenter and before the three-phase disc decanter.

5. The system of claim 4, wherein the fiber separation decanter receives a whole stillage and separates the whole stillage into a solid portion and a liquid portion.

6. The system of claim 5, wherein the liquid portion is received by the three-phase disc decanter.

7. The system of claim 1, wherein the three-phase disc decanter generates a cake phase discharge, wherein the three-phase disc decanter is coupled with a protein dryer.

8. The system of claim 7, wherein a back-set stream is sent back to a front-end process before the fermenter.

9. The system of claim 1, wherein the three-phase disc decanter generates a heavy phase comprises de-oiled germs and protein.

10. The system of claim 9, further comprising an evaporator receives the heavy phase from the three-phase disc decanter.

11. The system of claim 10, further comprising an oil recovery container receives an concentrated solution from the evaporator for oil recovery.

12. The system of claim 1, wherein the three-phase disc decanter generates a heavy phase, wherein the heavy phase is used as a back-set stream at a front-end process before the fermenter.

13. The system of claim 1, wherein the three-phase disc decanter generates a heavy phase, wherein the three-phase disc decanter is coupled an evaporator.

14. The system of claim 1, further comprising a germ/fiber separating container located between the fermenter and the three-phase disc decanter.

15. The system of claim 1, further comprising a decanter located between the fermenter and the three-phase disc decanter.

16. The system of claim 1, wherein the two different types of disc stocks comprise a clarified disc stock and a purified disc stock.

17. A back-end two centrifuges dry mill system comprising a fermenter, a three-phase disc decanter and an oil polishing centrifuge, wherein the three-phase disc decanter and the oil polishing centrifuge are after the fermenter, wherein the three-phase disc decanter has a disc height/disc diameter ratio greater than 1, and wherein the three-phase disc decanter comprises two different disc stocks.

* * * * *